(12) United States Patent
Zhou

(10) Patent No.: US 11,969,458 B2
(45) Date of Patent: *Apr. 30, 2024

(54) FORMULA OF NEUREGULIN PREPARATION

(71) Applicant: Zensun (Shanghai) Science & Technology, Co., Ltd., Shanghai (CN)

(72) Inventor: Mingdong Zhou, Shanghai (CN)

(73) Assignee: Zensun (Shanghai) Science & Technology, Co., Ltd., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/894,540

(22) Filed: Jun. 5, 2020

(65) Prior Publication Data

US 2021/0113661 A1 Apr. 22, 2021

Related U.S. Application Data

(63) Continuation of application No. 15/109,583, filed as application No. PCT/CN2014/094073 on Dec. 17, 2014, now Pat. No. 10,702,585.

(30) Foreign Application Priority Data

Jan. 3, 2014 (CN) .......................... 201410002665.6

(51) Int. Cl.
| | | |
|---|---|---|
| *A61K 38/18* | (2006.01) | |
| *A61K 9/08* | (2006.01) | |
| *A61K 9/16* | (2006.01) | |
| *A61K 9/19* | (2006.01) | |
| *A61K 47/02* | (2006.01) | |
| *A61K 47/42* | (2017.01) | |
| *C07K 14/475* | (2006.01) | |

(52) U.S. Cl.
CPC ............ *A61K 38/1883* (2013.01); *A61K 9/08* (2013.01); *A61K 9/1623* (2013.01); *A61K 9/19* (2013.01); *A61K 47/02* (2013.01); *A61K 47/42* (2013.01)

(58) Field of Classification Search
None
See application file for complete search history.

(56) References Cited

U.S. PATENT DOCUMENTS

| | | |
|---|---|---|
| 5,530,109 A | 6/1996 | Goodearl et al. |
| 5,716,930 A | 2/1998 | Goodearl et al. |
| 5,834,229 A | 11/1998 | Vandlen et al. |
| 6,054,261 A | 6/2000 | Masterson |
| 6,444,642 B1 | 9/2002 | Sklar et al. |
| 6,635,249 B1 | 10/2003 | Marchioni et al. |
| 6,750,196 B1 | 6/2004 | Reh et al. |
| 7,063,961 B2 | 6/2006 | Ballinger et al. |
| 7,115,554 B1 | 10/2006 | Sklar et al. |
| 7,141,077 B2 | 11/2006 | Detering et al. |
| 7,226,907 B1 | 6/2007 | Zhou |
| 7,612,164 B2 | 11/2009 | Zhou |
| 7,795,212 B2 | 9/2010 | Zhou |
| 7,964,555 B2 | 6/2011 | Zhou |
| 8,476,405 B2 | 7/2013 | Zhou |
| 8,609,620 B2 | 12/2013 | Zhou |
| 8,785,387 B2 | 7/2014 | Zhou |
| 9,012,400 B2 | 4/2015 | Zhou |
| 9,089,524 B2 | 7/2015 | Zhou |
| 9,198,951 B2 | 12/2015 | Caggiano et al. |
| 9,340,597 B2 | 5/2016 | Zhou |
| 9,434,777 B2 | 9/2016 | Zhou |
| 9,555,076 B2 | 1/2017 | Zhou |
| 9,580,515 B2 | 2/2017 | Zhou |
| 9,655,949 B2 | 5/2017 | Zhou |
| 10,098,834 B2 | 10/2018 | Zhou |
| 10,112,983 B2 | 10/2018 | Zhou |
| 10,441,633 B2 | 10/2019 | Zhou |
| 10,561,709 B2 | 2/2020 | Zhou |
| 2004/0126860 A1 | 7/2004 | Epstein et al. |
| 2006/0160062 A1 | 7/2006 | Young |
| 2006/0199767 A1 | 9/2006 | Zhou |
| 2007/0129296 A1 | 6/2007 | Zhou |
| 2007/0141548 A1 | 6/2007 | Kohl et al. |
| 2007/0190127 A1 | 8/2007 | Zhou |
| 2007/0213264 A1 | 9/2007 | Zhou |
| 2009/0105109 A1 | 4/2009 | Lant et al. |
| 2009/0156488 A1 | 6/2009 | Zhou |

(Continued)

FOREIGN PATENT DOCUMENTS

| | | |
|---|---|---|
| CN | 1276381 A | 12/2000 |
| CN | 1138785 C | 2/2004 |

(Continued)

OTHER PUBLICATIONS

Bakalets, "Chronic heart deficiency with preserved left ventricle ejection fraction," *Problems of Health and Ecology*, Gomel State Medical University, 3(33):7-11 (2012). English abstract.
Balligand et al., Cardiac endothelium and tissue growth, *Prog. Cardiovasc. Dis.*, 39(4):351-360 (1997).
Britsch et al., "The ErbB2 and ErbB3 receptors sand their ligand, neregulin-1, are essential for development of the sympathetic nervous system," *Genes Dev.*, 12:1825-1836 (1998).
Buonanno et al., "Neuregulin and ErbB receptor signaling pathways in the nervous system," *Curr. Opin. Neurobiol.*, 11:287-296 (2001).
Carraway et al., "Neuregulin-2, a new ligand of ErbB/ErbB4-receptor tyrosine kinase," *Nature*, 387:512-516 (1997).

(Continued)

*Primary Examiner* — Christine J Saoud
*Assistant Examiner* — Jon M Lockard
(74) *Attorney, Agent, or Firm* — Jones Day

(57) ABSTRACT

The present invention provides a pharmaceutical preparation for treating a cardiovascular disease. Particularly, the present invention provides a formula of a neuregulin pharmaceutical preparation. The formula consist of neuregulin polypeptide, a buffer, a stabilizer, an excipient, a salt, and another component, can ensure the long-term stability of the neuregulin polypeptide, and can be used for treating a heart failure patient or a patient in a risk of the heart failure.

26 Claims, 9 Drawing Sheets

Specification includes a Sequence Listing.

(56) References Cited

U.S. PATENT DOCUMENTS

| | | |
|---|---|---|
| 2011/0135595 A1 | 6/2011 | Zhou |
| 2011/0212108 A1 | 9/2011 | Takada |
| 2011/0229444 A1 | 9/2011 | Zhou |
| 2013/0078235 A1 | 3/2013 | Zhou |
| 2013/0196911 A1 | 8/2013 | Jay et al. |
| 2013/0259924 A1 | 10/2013 | Bancel et al. |
| 2014/0364366 A1 | 12/2014 | Zhou |
| 2015/0284440 A1 | 10/2015 | Zhou |
| 2016/0095903 A1 | 4/2016 | Zhou |
| 2016/0324876 A1 | 11/2016 | Zhou |
| 2017/0007671 A1 | 1/2017 | Zhou |
| 2017/0189489 A1 | 7/2017 | Zhou |
| 2017/0232068 A1 | 8/2017 | Zhou |
| 2017/0313784 A1 | 11/2017 | Zhou |
| 2017/0326204 A1 | 11/2017 | Zhou |
| 2017/0360889 A1 | 12/2017 | Zhou |
| 2017/0368140 A1 | 12/2017 | Zhou |
| 2018/0104311 A1 | 4/2018 | Zhou |
| 2019/0240145 A1 | 8/2019 | Zhou |

FOREIGN PATENT DOCUMENTS

| | | |
|---|---|---|
| CN | 1498656 A | 5/2004 |
| CN | 1768859 A | 5/2006 |
| CN | 1836731 A | 9/2006 |
| CN | 101310766 A | 11/2008 |
| CN | 101310779 A | 11/2008 |
| CN | 101394861 A | 3/2009 |
| RU | 2180843 C2 | 3/2002 |
| WO | WO 1989/01489 A | 2/1989 |
| WO | WO 1994/26298 A1 | 11/1994 |
| WO | WO 1997/09425 A1 | 3/1997 |
| WO | WO 99/18976 A1 | 4/1999 |
| WO | WO 00/37095 A1 | 6/2000 |
| WO | WO 00/64400 A2 | 11/2000 |
| WO | WO 00/78347 A1 | 12/2000 |
| WO | WO 2001/64877 A2 | 9/2001 |
| WO | WO 2001/89568 A1 | 11/2001 |
| WO | WO 2002/040683 A2 | 5/2002 |
| WO | WO 03/099300 A1 | 12/2003 |
| WO | WO 03/099320 A1 | 12/2003 |
| WO | WO 03/099321 A1 | 12/2003 |
| WO | WO 2004/050894 A2 | 6/2004 |
| WO | WO 2004/112763 A2 | 12/2004 |
| WO | WO 2005120547 | 12/2005 |
| WO | WO 2006/108208 A1 | 10/2006 |
| WO | WO 2007/062594 A1 | 6/2007 |
| WO | WO 2007/076701 A1 | 7/2007 |
| WO | WO 2008/028405 A1 | 3/2008 |
| WO | WO 2008/089994 A1 | 7/2008 |
| WO | WO 2009/033373 A1 | 3/2009 |
| WO | WO 2010/060265 A1 | 6/2010 |
| WO | WO 2010/060266 A1 | 6/2010 |
| WO | WO 2010/142141 A1 | 12/2010 |
| WO | WO 2011/091723 A1 | 8/2011 |
| WO | WO 2011/112864 A1 | 9/2011 |
| WO | WO 2012/012682 A2 | 1/2012 |
| WO | WO 2013/053076 A1 | 4/2013 |
| WO | WO 2013/053158 A1 | 4/2013 |
| WO | WO 2013/053201 A1 | 4/2013 |
| WO | WO 2014/056121 A1 | 4/2014 |
| WO | WO 2014/0138502 A1 | 9/2014 |
| WO | WO 2014/187342 A1 | 11/2014 |
| WO | WO 2015/010449 A1 | 1/2015 |
| WO | WO 2015/101182 A1 | 7/2015 |
| WO | WO 2015/101208 A1 | 7/2015 |
| WO | WO 2016/045493 A1 | 3/2016 |
| WO | WO2016/058493 A1 | 4/2016 |

OTHER PUBLICATIONS

Chang et al., "Ligands for ErbB-family receptors encoded by a neuregulin-like gene," *Nature*, 387:509-512 (1997).

Chen et al., "Expression and Regulation of Cardiotrophin-1 in Ischemia-1 Reinfusion Cardiac Muscle of Rats and Effect of Neuregulin-1," *J. Appl. Clin. Pediatr.*, 21(1):29-52 (2006).

Chien et al., "Regulation of cardiac gene expression during myocardial growth and hypertrophy: molecular studies of an adaptive physiologic response," *FASEB J.*, Dec. 1991; 5(15):3037-3046.

Chien, "Molecular advances in cardiovascular biology," *Science*, 260(5110):916-917 (1993).

Colucci et al., "Pathphysiology of heart failure," Chapter 13 in *Heart Diseases: A textbook of cardiovascular medicine*, Braunwald, ed., Saunders, Philadelphia. 1996; 5:394-420.

Crone et al., "ErbB2 is essential in the prevention of dilated cardiomyopathy," *Nat Med.*, 8(5):459-465 (2002).

Dias et al., "The molecular basis of skeletal muscle differentiation," *Semin Diagn Pathol.*, Feb. 1994; 11(1):3-14.

Eppstein et al., "Biological activity of liposome-encapsulated murine interferon gamma is mediated by a cell membrane receptor," *Proc. Natl. Acad. Sci. U S A.*, Jun. 1985; 82(11):3688-3692.

Falls et al., "Neuregulins: functions, forms, and signaling strategies," *Exp. Cell Res.*, 284(1):14-30 (2003).

Florini et al., "Stimulation of myogenic differentiation by a neuregulin, glial growth factor 2," *J. Biol. Chem.*, 271(22):12699-12702 (1996).

Galindo et al., "Anti-remodeling and anti-fibrotic effects of the neuregulin-1β glial growth factor 2 in a large animal model of heart failure," *J. Am. Heart Assoc.*, 3(5):e000773 (2014).

Gao et al., "A Phase II, randomized, double-blind, multicenter, based on standard therapy, placebo-controlled study of the efficacy and safety of recombinant human neuregulin-1 in patients with chronic heart failure," *J. Am. Coll. Cardiol.*, 55(18):1907-1914 (2010).

GENBANK Accession No. AJ247087, Apr. 15, 2005.

GENBANK Accession No. NM_001110810, Nov. 24, 2007.

Gu et al., "Cardiac functional improvement in rats with myocardial infarction by up-regulating cardiac myosin light chain kinase with neuregulin," *Cardiovasc. Res.*, 88(2):334-343 (2010).

Hein et al., "Altered expression of titin and contractile proteins in failing human myocardium," *J. Mol. Cell Cardiol.*, 26(10):1291-1306 (1994).

Higashiyama et al., "A novel brain-derived member of the epidermal growth factor family that interacts with ErbB3 and ErbB4," *J. Biochem.*, 122:675-680 (1997).

Hijazi et al., "NRG-3 in human breast cancers: activation of multiple erbB family proteins," *Int. J. Oncol.*, 13:1061-1067 (1998).

Holmes et al., "Identification of heregulin, a specific activator of $p185^{erbB2}$," *Science*, 256:1205-1210 (1992).

Hwang et al., "Hepatic uptake and degradation of unilamellar sphingomyelin/cholesterol liposomes: a kinetic study," *Proc. Natl. Acad. Sci. U S A.*, Jul. 1980; 77(7):4030-4034.

Izumo et al., "Calcineurin—the missing link in cardiac hypertrophy," *Nat. Med.*, 4(6):661-662 (1998).

Jones et al., "Binding interaction of the heregulinbeta egf domain with ErbB3 and ErbB4 receptors assessed by alanine scanning mutagenesis," *J. Biol. Chem.*, 273(19):11667-11674 (1998).

Kuramochi et al., "Cardiac endothelial cells regulate reactive oxygen species-induced cardiomyocyte apoptosis through neuregulin-1β/erbB4 signaling," *J. Biol. Chem.*, 279(49):51141-51147 (2004).

Langer et al., "Biocompatibility of polymeric delivery systems for macromolecules," *J. Biomed. Mater. Res.*, Mar. 1981; 15(2):267-277.

Liu et al., "Effects of neuregulin on Rhesus monkey heart failure induced by rapid pacing," *Sichuan Da Xue Xue Bao Yi Xue Ban*, 2009, 40(1):93-96 (in Chinese with English Abstract).

Liu et al., "Neuregulin-1/ErbB-activation improves cardiac function and survival in models of ischemic, dilated, and viral cardiomyopathy," *J. Am. Coll. Cardiol.*, 2006, 48(7):1438-1447.

Liu, "Protective effects of neuregulin-1β on chronic contractibility cardiac failure and correlative mechanisms research," Chinese Master's Thesis Full-text database, Medicine and Health Sciences, Jun. 2010, English abstract attached.

Luo et al., "Computational analysis of molecular basis of 1:1 interactions of NRG-1beta wild-type and variants with ErbB3 and ErbB4," *Proteins*, 59(4):742-756 (2005).

(56) References Cited

OTHER PUBLICATIONS

Mahmood et al., "Selection of the first-time dose in humans: comparison of different approaches based on interspecies scaling of clearance," *J. Clin. Pharm.*, 43:692-697 (2003).

Massova et al., "Computational alanine scanning to probe protein-protein interactions: a novel approach to evaluate binding fee energies," *J. Am. Chem. Soc.*, 121(36):8133-8143 (1999).

Ngo et al., "Computational complexity, protein structure prediction, and the Levinthal paradox," In Merz and Le Grand (Eds.), *The Protein Folding Problem and Tertiary Structure Prediction*. Birkhauser: Boston, pp. 491-495 (1994).

Olson et al., "Regulation of muscle transcription by the MyoD family. The heart of the matter," *Circ. Res.*, 72(1):1-6 (1993).

Parker et al., "p53-independent expression of p21Cip1 in muscle and other terminally differentiating cells," *Science*, 267(5200):1024-1027 (1995).

Physicians' Desk Reference. Medical Economics Data Production Co., Montvale, NJ. 1994; pp. 2314-2320.

Rumyantsev, "Interrelations of the proliferation and differentiation processes during cardiac myogenesis and regeneration," *Int. Rev. Cytol.*, 51:186-273 (1977).

Sawyer et al., "Modulation of anthracycline-induced myofibrillar disarray in rat ventricular myocytes by neuregulin-1beta and anti-erbB2: potential mechanism for trastuzumab-induced cardiotoxicity," *Circulation*, 105(13):1551-1554 (2002).

Schaper et al., "Impairment of the myocardial ultrastructure and changes of the cytoskeleton in dilated cardiomyopathy," *Circulation*, 83(2):504-514 (1991).

Sidman et al., "Controlled release of macromolecules and pharmaceuticals from synthetic polypeptides based on glutamic acid," *Biopolymers*, Jan. 1983; 22(1):547-556.

Simpson et al., "Myocyte hypertrophy in neonatal rat heart cultures and its regulation by serum and by catecholamines," *Circ. Res.* 51(6):787-801 (1982).

Slamon et al., "Use of chemotherapy plus a monoclonal antibody against HER2 for metastatic breast cancer that overexpresses HER2," *N. Engl. J. Med.*, 344(11):783-792 (2001).

Stevenson et al., "Optimizing therapy for complex or refractory heart failure: a management algorithm," *Am. Heart J.*, 135(6 Pt 2 Su):S293-S309 (1998).

Swynghedauw, "Molecular mechanisms of myocardial remodeling," *Physiol. Rev.*, 79(1):215-262 (1999).

U.S. Department of Health and Human Services, Food and Drug Administration, Center for Drug Evaluation and Research (CDER), "Guidance for Industry, estimating the maximum safe starting dose in initial clinical trials for therapeutics in adult heathy volunteers," Jul. 2005.

Wang et al., "Improvement of cardiac function and reversal of gap junction remodeling by Neuregulin-1β in volume-overloaded rats with heart failure," *J. Geriatr. Cardiol.*, 9(2):172-179 (2012).

Watson et al., *Molecular Biology of the Gene*, 4$^{the}$ Edition, The Bejacmin/Cummings Publishing Company, Inc., Menlo Park, CA, p. 224 (1987).

Wells, "Additivity of mutational effects in proteins," *Biochem.*, 29(37):8509-8517 (1990).

Yarden et al., "Untangling the ErbB signaling network," *Nat. Rev. Mol. Cell Biol.*, 2(2):127-137 (2001).

Zhao et al., "Selective disruption of neuregulin-1 function in vertebrate embryos using ribozyme-tRNA transgenes," *Development*, May 1998; 125(10):1899-1907.

Zhao et al., "Neuregulins promote survival and growth of cardiac myocytes. Persistence of ErbB2 and ErbB4 expression in neonatal and adult ventricular myocytes," *J. Biol. Chem.*, 273(17):10261-10269 (1998).

Zhou et al., "Retinoid-dependent pathways suppress myocardial cell hypertrophy," *Proc. Natl. Acad. Sci. USA.*, Aug. 1, 1995; 92(16):7391-7395.

Akers et al., "Peptides and Proteins as Parenteral Solutions," Pharmaceutical Formulation Development of Peptides and Proteins, 2:149-192 (2013).

Bak et al., "Physicochemical and Formulation Development Assessment for Therapeutic Peptide Delivery—A Primer," The AAPS Journal 17(1):144-155 (2014).

Cell Signaling Technology #5218, "Human Neuregulin-1 (hNRG-1)".

Genome Quest Search, Opposition to European Patent No. 3,090,756 B1.

Ioannou et al., "Treatment with a combination of the ErbB (HER) family blocker afatinib and the IGF-IR inhibitor, NVP-AEW541 induces synergistic growth inhibition of human pancreatic cancer cells," BMC Cancer 13(41):1-12 (2013).

Liu et al., "RNAi-mediated inhibition of presenilin 2 inhibits glioma cell growth and invasion and is involved in the regulation of Nrg1 / ErbB signaling," Neuro-Oncology 14(8):994-1006 (2012).

Manning et al., "Stability of Protein Pharmaceuticals: An Update," Pharmaceutical Research 27(4):544-575 (2010).

Mendes-Ferreira, "Therapeutic potential of neuregulin-1 in cardiovascular disease," Drug Discovery Today 18:836-842 (2013).

Perez-Ramirez, "Preformulation Research: Assessing Protein Solution Behavior During Early Development," 119-146 (2010).

Zhang et al., "A Notch1-neuregulin1 autocrine signaling loop contributes to melanoma growth," Oncogene 31:4609-4618 (2012).

Stawman Limited, Statement of Grounds of Opposition to the Grant of European Patent No. 3 090 756, filed Jun. 30, 2021 (48 pages).

Zensun (Shanghai) Science & Technology, Co., Ltd., Letter from the Proprietor of the Patent of Nov. 22, 2021, in the Matter of Opposition to European Patent No. 3 090 756 (12 pages, with 9 additional pages of enclosures).

European Patent Office, Preliminary and Non-Binding Opinion of the Opposition Division, dated Feb. 23, 2023, in the Matter of Opposition to European Patent No. 3 090 756 (11 pages).

FORMULA OF NEUREGULIN PREPARATION

CROSS-REFERENCE TO RELATED APPLICATIONS

This application is a U.S. non-provisional application, which is a continuation of U.S. application Ser. No. 15/109,583 filed on Jul. 1, 2016, and now granted as U.S. Pat. No. 10,702,585; which is a U.S. national stage application of PCT/CN2014/094073, having an international filing date of Dec. 17, 2014, which claims the benefit of priority of Chinese application No. 201410002665.6, filed Jan. 3, 2014, the entire contents of each of which are incorporated herein by reference.

FIELD OF THE INVENTION

Generally, the invention relates to pharmaceutical preparations for the treatment of cardiovascular disease, for example heart failure. In particular, this invention relates to formula of neuregulin preparations.

SEQUENCE LISTING

This application incorporates by reference in its entirety the Computer Readable Form of a Sequence Listing in ASCII text format submitted via EFS-Web. The Sequence Listing text file submitted via EFS-Web is entitled "11748-092-999_SequenceListing.TXT," created on Jun. 4, 2020 and is 1,592 bytes in size.

BACKGROUND

Heart failure affects approximately five million Americans, and more than 550,000 new patients are diagnosed with the condition each year. Current drug therapy for heart failure is primarily directed to angiotensin-converting enzyme (ACE) inhibitors, which are vasodilators that cause blood vessels to expand, lowering blood pressure and reducing the heart's workload. While the percent reduction in mortality has been significant, the actual reduction in mortality with ACE inhibitors has averaged only 3%-4%, and there are several potential side effects. Additional limitations are associated with other options for preventing or treating heart failure. For example, heart transplantation is clearly more expensive and invasive than drug treatment, and it is further limited by the availability of donor hearts. Use of mechanical devices, such as biventricular pacemakers, is similarly invasive and expensive. Thus, there has been a need for new therapies given the deficiencies in current therapies.

One promising new therapy involves administration of neuregulin (hereinafter referred to as "NRG") to a patient suffering from or at risk of developing heart failure. NRGs, a family of EGF-like growth factors, comprises a family of structurally related growth and differentiation factors that include NRG1, NRG2, NRG3 and NRG4 and isoforms thereof, are involved in an array of biological responses: stimulation of breast cancer cell differentiation and secretion of milk proteins; induction of neural crest cell differentiation to Schwann cells; stimulation of skeletal muscle cell synthesis of acetylcholine receptors; and, promotion of myocardial cell survival and DNA synthesis. In vivo studies of neuregulin gene-targeted homozygous mouse embryos with severe defects in ventricular trabeculae formation and dorsal root ganglia development indicate that neuregulin is essential for heart and neural development.

NRGs bind to the EGF receptor family, which comprises EGFR, ErbB2, ErbB3 and ErbB4, each of which plays an important role in multiple cellular functions, including cell growth, differentiation and survival. They are protein tyrosine kinase receptors, consisting of an extracellular ligand-binding domain, transmenbrane kinase domain and cytoplasmic tyrosine kinase domain. After NRG bind to the extracellular domain of ErbB3 or ErbB4, it induces a conformational change that leads to heterodimer formation between ErbB3, ErbB4 and ErbB2 or homodimer formation between ErbB4 itself, which results in phosphorylation of the receptor's C-terminal domain inside the cell membrane. The phosphorylated intracellular domain then binds additional signal proteins inside the cell, activating the corresponding downstream AKT or ERK signaling pathway, and inducing a series of cell reactions, such as stimulation or depression of cell proliferation, cell differentiation, cell apoptosis, cell migration or cell adhesion. Among these receptors, mainly ErbB2 and ErbB4 are expressed in the heart.

It has been shown that the EGF-like domains of NRG-1, ranging in size from 50 to 64-amino acids, are sufficient to bind to and activate these receptors. Previous studies have shown that neuregulin-10 (NRG-10) can bind directly to ErbB3 and ErbB4 with high affinity. The orphan receptor, ErbB2, can form heterodimer with ErbB3 and ErbB4 with higher affinity than ErbB3 or ErbB4 homodimers. Research in neural development has indicated that the formation of the sympathetic nervous system requires an intact NRG-1β, ErbB2 and ErbB3 signaling system. Targeted disruption of the NRG-1β or ErbB2 or ErbB4 led to embryonic lethality due to cardiac development defects. Recent studies also highlighted the roles of NRG-1β, ErbB2 and ErbB4 in the cardiovascular development as well as in the maintenance of adult normal heart function. NRG-1B has been shown to enhance sarcomere organization in adult cardiomyocytes. The administration of a recombinant NRG-1B EGF-like domain significantly improves or protects against deterioration in myocardial performance in distinct animal models of heart failure as well as in clinical trials. These results make NRG-1 promising as a broad spectrum therapeutic or lead compound for heart failure due to a variety of common diseases. Mostly, pharmaceutical protein formulations are intended to be administered in the form of injections. However, it is common knowledge that there exist some active proteins which present stability problems. Thus there exists a need in the art to develop a stable pharmaceutical formulation comprising NRG.

SUMMARY OF THE INVENTION

The present invention provides a pharmaceutical formulation of neuregulin (NRG) comprising: (a) a NRG polypeptide; (b) a buffering agents, wherein said formulation has a pH between 3-7. In some embodiments, the NRG formulation further comprises: (c) a stabilizing agent. In some embodiments, the NRG formulation further comprises: (d) a salt. In some embodiments, the formulation is a liquid formulation. In some embodiments, the formulation is a lyophilized formulation.

The NRG polypeptide in the formulations provided herein is selected from the group consisting of: a) a polypeptide comprising the amino acid sequence set forth in SEQ ID NO: 2; b) a polypeptide comprising a EGF like domain of NRG; c) a biologically active analog, fragment or variant of the polypeptide of a); d) a polypeptide encoded by the polynucleotide set forth in SEQ ID NO: 1; e) a biologically active analog, fragment or variant of the polypeptide of d); and f) a polypeptide encoded by a polynucleotide that hybridizes to the polynucleotide set forth in SEQ ID NO: 1 under moderately stringent hybridization conditions. In some embodiments, the NRG polypeptide is a polypeptide consisting of the amino acid sequence set forth in SEQ ID NO: 2. In some embodiments, the concentration of NRG polypeptide is in a range of about 0.01 g/L to about 1 g/L. In additional embodiments, the NRG polypeptide in the formulations provided by the invention is a polypeptide consisting of the amino acid sequence set forth in SEQ ID NO: 2 at a concentration of about 0.25 g/L.

In some embodiments, the formulations provided by the invention comprise a pH buffering agent. In related embodiments, the pH buffering agent is in a range of about 0.1 mM to about 500 mM. The buffering agent is selected from the group consisting of citrate, phosphate, acetate, histidine, glycine, bicarbonate, HEPES, Tris, diluted HCl, diluted NaOH or combinations of these agents. In one embodiment, the buffering agent in the formulation provided by the invention is phosphate. In some embodiments, the formulation of the invention has a pH of about 6.0. In some embodiments, the formulation of the invention has a pH of about 3.4.

In some embodiments, the formulations provided by the invention comprise a stabilizing agent. In further embodiments, the formulations provided by the invention are at a concentration of about 0.1 g/L to about 200 g/L. In additional embodiments, the stabilizing agent is selected from the group consisting of mannitol, sorbitol, xylitol, sucrose, trehalose, mannose, maltose, lactose, glucose, raffinose, cellobiose, gentiobiose, isomaltose, arabinose, glucosamine, fructose, human serum albumin and combinations of these stabilizing agents. In some embodiments, the stabilizing agent is human serum albumin at a concentration of about 2 g/L.

In additional embodiments, the formulations provided by the invention comprise a salt. In some embodiments the salt is at a concentration range of about 100 mM to about 500 mM. In a particular embodiment, the salt is sodium chloride. In a related embodiment, the concentration of salt in a formulation of the invention is about 150 mM.

In some embodiments, the NRG polypeptide in the formulation provided by the invention consists of the amino acid sequence set forth in SEQ ID NO: 2; wherein the buffering agent is phosphate at a concentration of 10 mM, and wherein the pH is about 6.0.

In some embodiments, the NRG polypeptide in the formulation provided by the invention is a polypeptide consisting of the amino acid sequence set forth in SEQ ID NO: 2 at a concentration of about 0.25 g/L, the buffering agent is phosphate at a concentration of about 10 mM, said PH is about 6.0, the stabilizing agent is human serum albumin at a concentration of about 2 g/L, and the salt is sodium chloride at a concentration of about 150 mM.

In some embodiments, the formulation provided by the invention is a liquid pharmaceutical formulation. In additional embodiments, the NRG polypeptide in the NRG liquid pharmaceutical formulation provided by the invention is a polypeptide consisting of the amino acid sequence set forth in SEQ ID NO: 2 at a concentration of about 0.25 g/L, the buffering agent is phosphate at a concentration of about 10 mM, said PH is about 3.4.

In some embodiments, the formulation provided by the invention is a lyophilized pharmaceutical formulation of NRG, prepared by lyophilization of any of above-mentioned formulations added with an excipient. In some embodiments, the excipient is selected from the group consisting of human serum albumin, mannitol, glycine, polyethylene glycol, and combinations of these excipients. In a specific embodiment, the excipient is mannitol. In relevant embodiments, the excipient is at a concentration of about 0.1 g/L to about 200 g/L after resuspension of about 60 mg of the formulation with 1 ml of a resuspension solution. In a specific embodiment, mannitol is at a concentration of about 50 g/L after resuspension of about 60 mg of the formulation with 1 ml of a resuspension solution.

In further embodiments, the invention provides a lyophilized pharmaceutical formulation of neuregulin (NRG) comprising: (a) a NRG polypeptide; (b) a buffering agent, and (c) an excipient. In additional embodiments, the lyophilized pharmaceutical formulation further comprises a stabilizing agent. In additional embodiments, the lyophilized pharmaceutical formulation further comprises a salt.

In a specific embodiment, the lyophilized pharmaceutical formulation of the invention comprises (a) a polypeptide consisting of the amino acid sequence set forth in SEQ ID NO: 2, (b) phosphate as the buffering agent, (c) mannitol as the excipient, (d) human serum albumin as the stabilizing agent, and (e) sodium chloride as the salt, wherein after resuspension of about 60 mg of the formulation with 1 ml of a resuspension solution, (a) is at a concentration of about 0.25 g/L; (b) is at a concentration of about 10 mM, and wherein the pH is about 6; (c) is at a concentration of about 50 g/L, (d) is at a concentration of about 2 g/L, and (e) is at a concentration of about 150 mM.

DETAILED DESCRIPTION OF THE INVENTION

Figure 1:
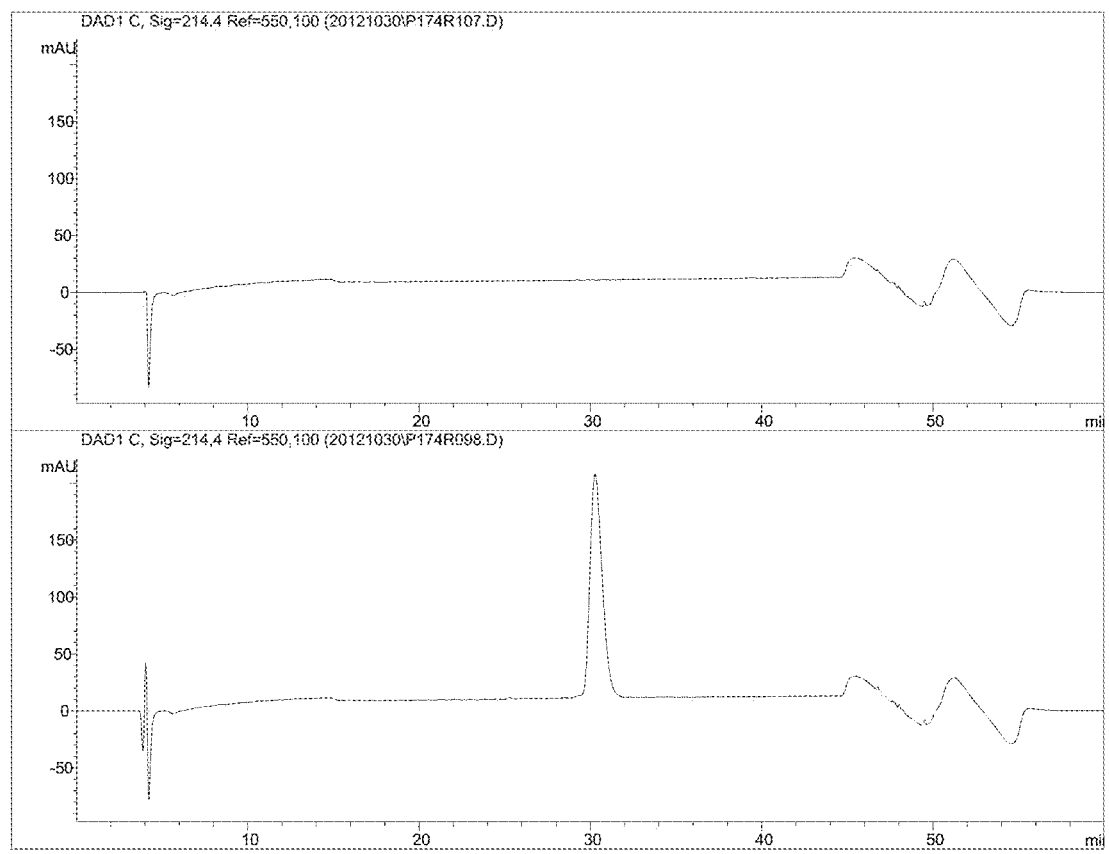
FIG. 1: Representative chromatograms of the recombinant human Neuregulin-1 (rhNRG-1) Diluent and standard solution prepared at 0.25 mg/mL in the Diluent

The present disclosure is based, in part, on the discovery that particular pharmaceutical formulations of neuregulin achieve surprising and unexpected stability of the neuregulin polypeptide. In this regard, it was discovered that an unexpected improvement in stability can be achieved by adapting a lower pH for a neuregulin formulation of the invention. Although any methods similar or equivalent to those described herein can be used in the practice of the present invention, the preferred methods and materials are now described.

As used in this specification and the appended claims, the singular forms "a", "an" and "the" include plural referents unless the content clearly dictates otherwise. Thus, for example, reference to "a buffering agent" includes a mixture of two or more buffering agents, and the like.

The term "about," particularly in reference to a given quantity, is meant to encompass deviations of plus or minus ten percent.

As used in this application, including the appended claims, the singular forms "a," "an," and "the" include plural references, unless the content clearly dictates otherwise, and are used interchangeably with "at least one" and "one or more."

As used herein, the terms "comprises," "comprising," "includes," "including," "contains," "containing," and any variations thereof, are intended to cover a non-exclusive inclusion, such that a process, method, product-by-process, or composition of matter that comprises, includes, or contains an element or list of elements does not include only those elements but can include other elements not expressly listed or inherent to such process, method, product-by-process, or composition of matter.

As used herein a "polypeptide" refers to a polymer composed of amino acid residues, structural variants, related naturally-occurring structural variants, and synthetic non-naturally occurring analogs thereof linked via peptide bonds. Synthetic polypeptides are prepared, for example, using an automated polypeptide synthesizer. The term "protein" typically refers to large polypeptides. The term "peptide" typically refers to short polypeptides.

As used herein, "protein" is synonymous with "polypeptide" or "peptide" unless the context clearly dictates otherwise.

As used herein a "fragment" of a polypeptide is meant to refer to any portion of a polypeptide or protein smaller than the full-length polypeptide or protein expression product.

As used herein an "analog" refers to any of two or more polypeptides substantially similar in structure and having the same biological activity, but can have varying degrees of activity, to either the entire molecule, or to a fragment thereof. Analogs differ in the composition of their amino acid sequences based on one or more mutations involving substitution, deletion, insertion and/or addition of one or more amino acids for other amino acids. Substitutions can be conservative or non-conservative based on the physico-chemical or functional relatedness of the amino acid that is being replaced and the amino acid replacing it.

As used herein a "variant" refers to a polypeptide, protein or analog thereof that is modified to comprise additional chemical moieties not normally a part of the molecule. Such moieties may modulate the molecule's solubility, absorption, biological half-life, etc. The moieties may alternatively decrease the toxicity of the molecule and eliminate or attenuate any undesirable side effect of the molecule, etc. Moieties capable of mediating such effects are disclosed in Remington's Pharmaceutical Sciences (1980). Procedure for coupling such moieties to a molecule are well known in the art. For example and without limitation, in one aspect the variant is a blood clotting factor having a chemical modification which confers a longer half-life in vivo to the protein. In various aspects, polypeptides are modified by glycosylation, pegylation, and/or polysialylation.

Polynucleotides encoding fragments, variants and analogs may be readily generated by a worker of skill to encode biologically active fragments, variants, or analogs of the naturally-occurring molecule that possess the same or similar biological activity to the naturally-occurring molecule. In various aspects, these polynucleotides are prepared using PCR techniques, digestion/ligation of DNA encoding molecule, and the like. Thus, one of skill in the art will be able to generate single base changes in the DNA strand to result in an altered codon and a missense mutation, using any method known in the art, including, but not limited to site-specific mutagenesis. As used herein, the phrase "moderately stringent hybridization conditions" means, for example, hybridization at 42.degree. C. in 50% formamide and washing at 60.degree. C. in 0.1.times.SSC, 0.1% SDS. It is understood by those of skill in the art that variation in these conditions occurs based on the length and GC nucleotide base content of the sequences to be hybridized. Formulas standard in the art are appropriate for determining exact hybridization conditions. See Sambrook et al., 9.47-9.51 in Molecular Cloning, Cold Spring Harbor Laboratory Press, Cold Spring Harbor, N.Y. (1989).

As used herein, "heart failure" means an abnormality of cardiac function where the heart does not pump blood at the rate needed for the requirements of metabolizing tissues. Heart failure includes a wide range of disease states such as congestive heart failure, myocardial infarction, tachyarrhythmia, familial hypertrophic cardiomyopathy, ischemic heart disease, idiopathic dilated cardiomyopathy, myocarditis and the like. The heart failure can be caused by any number of factors, including, without limitation, ischemic, congenital, rheumatic, viral, toxic or idiopathic forms. Chronic cardiac hypertrophy is a significantly diseased state which is a precursor to congestive heart failure and cardiac arrest.

As used herein, "neuregulin" or "NRG" used in the present invention refers to proteins or peptides that can bind and activate ErbB2, ErbB3, ErbB4, or a homodimer or heterodimer thereof, including but not limited to all neuregulin isoforms, neuregulin EGF domain alone, polypeptides comprising neuregulin EGF-like domain, neuregulin mutants or derivatives, and any kind of neuregulin-like gene products that also activate the above receptors as described in detail below. Neuregulin also includes NRG-1, NRG-2, NRG-3 and NRG-4 proteins, peptides, fragments and compounds that mimic the activities of neuregulin. A neuregulin used in the present invention can activate the above ErbB receptors and modulate their biological reactions, e.g., stimulate acetylcholine receptor synthesis in skeletal muscle cell; and/or improve cardiocyte differentiation, survival and DNA synthesis. Neuregulin also includes those variants with conservative amino acid substitutions that do not substantially alter their biological activity. Suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson et al., Molecular Biology of the Gene, 4th Edition, 1987, Benjamin Cummings, p.224). In preferred embodiments, neuregulin used in the present invention refers to proteins or peptides that can bind to and activate ErbB2/ErbB4 or ErbB2/ErbB3 heterodimers, for example, but not for the purpose of restriction, peptides including the 177-237 fragment of NRG-1 β2 isoform containing EGF-like domain. The amino acid sequence of the fragment consists of:

(SEQ ID NO: 2)
SHLVKCAEKEKTFCVNGGECFMVKDLSNPSR

YLCKCPNEFTGDRCQNYVMASFYKAEELYQ.

As used herein, "epidermal growth factor-like domain" or "EGF-like domain" refers to a polypeptide motif encoded by the neuregulin gene that binds to and activates ErbB2, ErbB3, ErbB4, or a homodimer or heterodimer thereof, and bears a structural similarity to the EGF receptor-binding domain as disclosed in WO 00/64400, Holmes et al., Science, 256:1205-1210 (1992); U.S. Pat. Nos. 5,530,109 and 5,716,930; Hijazi et al., Int. J. Oncol., 13:1061-1067 (1998); Chang et al., Nature, 387:509-512 (1997); Carraway et al., Nature, 387:512-516 (1997); Higashiyama et al., J. Biochem., 122:675-680 (1997); and WO 97/09425, the contents of which are all incorporated herein by reference. In certain embodiments, EGF-like domain binds to and activates ErbB2/ErbB4 or ErbB2/ErbB3 heterodimers. In certain embodiments, EGF-like domain comprises the amino acid sequence of the receptor binding domain of NRG-1. In some embodiments, EGF-like domain comprises the amino acid sequence corresponding to amino acid residues 177-226, 177-237, or 177-240 of NRG-1. In certain embodiments, EGF-like domain comprises the amino acid sequence of the receptor binding domain of NRG-2. In certain embodiments, EGF-like domain comprises the amino acid sequence of the receptor binding domain of NRG-3. In certain embodiments, EGF-like domain comprises the amino acid sequence of the receptor binding domain of NRG-4. In certain embodiments, EGF-like domain comprises the amino acid sequence of Ala Glu Lys Glu Lys Thr Phe Cys Val Asn Gly Gly Glu Cys Phe Met Val Lys Asp Leu Ser Asn Pro, as described in U.S. Pat. No. 5,834,229.

The present invention provides NRG formulations, resulting in highly stable pharmaceutical compositions. The stable pharmaceutical compositions are useful as therapeutic agents in the treatment of individuals suffering from or at risk of developing heart failure.

In one embodiment, a pharmaceutical formulation of NRG is provided comprising: (a) NRG protein or polypeptide; (b) one or more buffering agents; the NRG protein or polypeptide is selected from the group consisting of: a) a protein or polypeptide comprising the amino acid sequence set forth in SEQ ID NO: 2; b) a NRG protein comprising EGF-like domain of NRG; c) a biologically active analog, fragment or variant of the polypeptide of a); d) a polypeptide encoded by the polynucleotide set forth in SEQ ID NO: 1; e) a biologically active analog, fragment or variant of the polypeptide of d); and f) a polypeptide encoded by a polynucleotide that hybridizes to the polynucleotide set forth in SEQ ID NO: 1 under moderately stringent hybridization conditions; the concentration of NRG protein or polypeptide is in the range of about 0.01 g/L to about 1 g/L; In some preferred embodiments, the concentration is in the range of about 0.01 g/L to about 0.8 g/L, about 0.01 g/L to about 0.6 g/L, about 0.01 g/L to about 0.4 g/L, about 0.01 g/L to about 0.2 g/L. In additional embodiments the NRG protein or polypeptide can be about 1.0 g/L, about 0.90 g/L, about 0.80 g/L, about 0.70 g/L, about 0.60 g/L, about 0.50 g/L, about 0.45 g/L, about 0.40 g/L, about 0.35 g/L, about 0.30 g/L, about 0.25 g/L, about 0.20 g/L, about 0.15 g/L, about 0.10 g/L, about 0.05 g/L or less.

In one preferred embodiment, the NRG protein or polypeptide is at a concentration of 0.25 g/L; the buffering agent is a pH buffering agent in a range of about 0.1 mM to about 500 mM and said pH is in a range of about 2.0 to about 12.0; the buffering agent is selected from the group consisting of citrate, phosphate, acetate, histidine, glycine, bicarbonate, HEPES, Tris, diluted HCl, diluted NaOH and combinations of these agents. In some preferred embodiments, the pH is in the range of about 3.0 to about 10.0, about 3.0 to about 7.0, about 2.3 to 3.8. In some embodiments the pH value is about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9 or about 4.0, about 4.1, about 4.2, about 4.3, about 4.4, about 4.5, about 4.6, about 4.7, about 4.8, about 4.9 or about 5.0, about 5.1, about 5.2, about 5.3, about 5.4, about 5.5, about 5.6, about 5.7, about 5.8, about 5.9 or about 6.0. In one preferred embodiment, the buffering agent is phosphate, the pH value is about 6. In one preferred embodiment, the buffering agent is phosphate, the pH value is about 3 to about 4. In another preferred embodiment, the buffering agent is phosphate, the pH value is about 3.4.

In one specific embodiment of the invention, the NRG formulation comprises a NRG polypeptide having the amino acid sequence set forth in SEQ ID NO: 2; a buffering agent is phosphate and the pH is about 6.0. In one specific embodiment of the invention, the NRG formulation comprises a NRG polypeptide having the amino acid sequence set forth in SEQ ID NO: 2; a buffering agent is phosphate and the pH is about 3.4.

In another embodiment, a stable pharmaceutical formulation of NRG is provided comprising: (a) NRG protein or polypeptide; (b) one or more buffering agents; and (c) one or more stabilizing agents; the stabilizing agents is selected from the group consisting of mannitol, sorbitol, xylitol, sucrose, trehalose, mannose, maltose, lactose, glucose, raffinose, cellobiose, gentiobiose, isomaltose, arabinose, glucosamine, fructose human serum albumin and combinations of these stabilizing agents; the stabilizing agents is at a concentration of about 0.1 g/L to about 200 g/L. In some preferred embodiments, the stabilizing agent is mannitol at a concentration of about 50 g/L. In some preferred embodiments, the stabilizing agent is human serum albumin at a concentration of about 2 g/L to about 8 g/L.

In one specific embodiment of the invention, the NRG formulation comprises a NRG polypeptide having the amino acid sequence set forth in SEQ ID NO: 2; a buffering agent is phosphate at a concentration of about 10 mM at about pH 6.0; a stabilizing agent is human serum albumin at a concentration of about 2 g/L.

In still another embodiment, a stable pharmaceutical formulation of NRG is provided comprising: (a) NRG protein or polypeptide; (b) one or more buffering agents; and (c) one or more excipients; the one or more excipients is selected from the group consisting of human serum albumin, mannitol, glycine, polyethylene glycol and combinations of these excipients; the one or more excipients is at a concentration of about 0.1 g/L to about 200 g/L. In some preferred embodiments, the excipient is human serum albumin at a concentration of about 2 g/L to about 8 g/L. In some preferred embodiments, the excipient is mannitol at a concentration of about 50 g/L.

In still another embodiment, a stable pharmaceutical formulation of NRG is provided comprising: (a) NRG protein or polypeptide; (b) one or more buffering agents; (c) one or more stabilizing agents; and (d) one or more excipients. In some preferred embodiments, the stabilizing agent is human serum albumin. In some preferred embodiments, the excipient is mannitol.

In still another embodiment, a stable pharmaceutical formulation of NRG is provided comprising: (a) NRG protein or polypeptide; (b) one or more buffering agents; (c) one or more stabilizing agents; (d) one or more excipients; and (e) one or more salts.

In some embodiments, the formulation provided by the invention is a lyophilized pharmaceutical formulation, prepared by lyophilization of any of above-mentioned formulations added with an excipient. In some embodiments, the excipient is selected from the group consisting of human serum albumin, mannitol, glycine, polyethylene glycol, and combinations of these excipients. In a specific embodiment, the excipient is mannitol.

In another embodiments, the lyophilized pharmaceutical formulation of neuregulin comprises: (a) NRG protein or polypeptide; (b) one or more buffering agents; (c) one or more excipients; (d) one or more stabilizing agents; and (e) one or more salts, wherein after resuspension of about 60 mg of the formulation with 1 ml of a resuspension solution, (a) is at a concentration of about 0.01 g/L to 1 g/L; (b) is at a concentration of about 0.1 mM to about 500 mM, and wherein the pH is about 3 to about 7; (c) is at a concentration of about 0.1 g/L to about 200 g/L, (d) is at a concentration of about 0.1 g/L to about 200 g/L, and (e) is at a concentration of about 100 mM to about 500 mM.

In one specific embodiment, the lyophilized pharmaceutical formulation provided by the invention comprises (a) a polypeptide consisting of the amino acid sequence set forth in SEQ ID NO: 2, (b) phosphate as the buffering agent, (c) mannitol as the excipient, (d) human serum albumin as the stabilizing agent, and (e) sodium chloride as the salt, wherein after resuspension of about 60 mg of the formulation with 1 ml of a resuspension solution, (a) is at a concentration of about 0.25 g/L; (b) is at a concentration of about 10 mM, and wherein the pH is about 6; (c) is at a concentration of about 50 g/L, (d) is at a concentration of about 2 g/L, and (e) is at a concentration of about 150 mM.

Lyophilization

In one aspect, the formulations comprising a NRG polypeptide of the invention can be prepared to a lyophilized pharmaceutical formulation by lyophilization. Lyophilization is carried out using techniques common in the art and should be optimized for the composition being developed [Tang et al., Pharm Res. 21:191-200, (2004) and Chang et al., Pharm Res. 13:243-9 (1996)].

A lyophilization cycle is, in one aspect, composed of three steps: freezing, primary drying, and secondary drying [A. P. Mackenzie, Phil Trans R Soc London, Ser B, Biol 278:167 (1977)]. In the freezing step, the solution is cooled to initiate ice formation. Furthermore, this step induces the crystallization of the bulking agent. The ice sublimes in the primary drying stage, which is conducted by reducing chamber pressure below the vapor pressure of the ice, using a vacuum and introducing heat to promote sublimation. Finally, adsorbed or bound water is removed at the secondary drying stage under reduced chamber pressure and at an elevated shelf temperature. The process produces a material known as a lyophilized cake. Thereafter the cake can be reconstituted with either sterile water or suitable diluent for injection.

The lyophilization cycle not only determines the final physical state of excipients but also affects other parameters such as reconstitution time, appearance, stability and final moisture content. The composition structure in the frozen state proceeds through several transitions (e.g., glass transitions, wettings, and crystallizations) that occur at specific temperatures and the structure may be used to understand and optimize the lyophilization process. The glass transition temperature (Tg and/or Tg') can provide information about the physical state of a solute and can be determined by differential scanning calorimetry (DSC). Tg and Tg' are an important parameter that must be taken into account when designing the lyophilization cycle. For example, Tg' is important for primary drying. Furthermore, in the dried state, the glass transition temperature provides information on the storage temperature of the final product.

Buffers and Buffering Agents

As used herein, "buffer" or "buffering agent" encompasses those agents or combinations of agents which maintain the solution pH in an acceptable range from about 2.0 to about 9.0. Suitable buffers are those that are not chemically reactive with other ingredients and are present in amounts sufficient to provide the desired degree of pH buffering.

The stability of a pharmacologically active protein formulation is usually observed to be maximal in a narrow pH range. This pH range of optimal stability needs to be identified early during pre-formulation studies. Several approaches, such as accelerated stability studies and calorimetric screening studies, are useful in this endeavor (Remmele R. L. Jr., et al., Biochemistry, 38(16): 5241-7 (1999)). Once a formulation is finalized, the protein must be manufactured and maintained throughout its shelf-life. Hence, buffering agents are almost always employed to control pH in the formulation.

The buffer capacity of the buffering species is maximal at a pH equal to the pKa and decreases as pH increases or decreases away from this value. Ninety percent of the buffering capacity exists within one pH unit of its pKa. Buffer capacity also increases proportionally with increasing buffer concentration.

Several factors need to be considered when choosing a buffer. First and foremost, the buffer species and its concentration need to be defined based on its pKa and the desired formulation pH. Equally important is to ensure that the buffer is compatible with the protein and other formulation excipients, and does not catalyze any degradation reactions. A third important aspect to be considered is the sensation of stinging and irritation the buffer may induce upon administration. For example, citrate is known to cause stinging upon injection (Laursen T, et al., Basic Clin Pharmacol Toxicol., 98(2): 218-21 (2006)). The potential for stinging and irritation is greater for drugs that are administered via the subcutaneous (SC) or intramuscular (IM) routes, where the drug solution remains at the site for a relatively longer period of time than when administered by the IV route where the formulation gets diluted rapidly into the blood upon administration. For formulations that are administered by direct IV infusion, the total amount of buffer (and any other formulation component) needs to be monitored. One has to be particularly careful about potassium ions administered in the form of the potassium phosphate buffer, which can induce cardiovascular effects in a patient (Hollander-Rodriguez J C, et al., Am. Fam. Physician., 73(2): 283-90 (2006)).

Buffers for lyophilized formulations need additional consideration. Some common buffers such as acetate and imidazole may sublime or evaporate during the lyophilization process, thereby shifting the pH of formulation during lyophilization or after reconstitution.

The buffer system present in the compositions is selected to be physiologically compatible and to maintain a desired pH of the pharmaceutical formulation. In one embodiment, the pH of the solution is between pH 2.0 and pH 12.0. For example, the pH of the solution can be, for example, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, or 12.0.

The pH buffering compound may be present in any amount suitable to maintain the pH of the formulation at a predetermined level. In one embodiment, the pH buffering concentration is between 0.1 mM and 500 mM. For example, it is contemplated that the pH buffering agent is at least 0.1, 0.5, 0.7, 0.8 0.9, 1.0, 1.2, 1.5, 1.7, 2, 3, 4, 5, 6, 7, 8, 9, 10, 11, 12, 13, 14, 15, 16, 17, 18, 19, 20, 25, 30, 40, 50, 60, 70, 80, 90, 100, 200, 300, or 500 mM.

Exemplary pH buffering agents used to buffer the formulation as set out herein include, but are not limited to organic acids, glycine, histidine, glutamate, succinate, phosphate, acetate, citrate, Tris, HEPES, and amino acids or mixtures of amino acids, including, but not limited to aspartate, histidine, and glycine. In one embodiment of the present invention, the buffering agent is phosphate.

Stabilizers and Bulking Agents

In one aspect of the present pharmaceutical formulations, a stabilizer (or a combination of stabilizers) is added to prevent or reduce storage-induced aggregation and chemical degradation. A hazy or turbid solution upon reconstitution indicates that the protein has precipitated or at least aggregated. The term "stabilizer" means an excipient capable of preventing aggregation or physical degradation, including chemical degradation (for example, autolysis, deamidation, oxidation, etc.) in an aqueous state. Stabilizers contemplated include, but are not limited to, sucrose, trehalose, mannose, maltose, lactose, glucose, raffinose, cellobiose, gentiobiose, isomaltose, arabinose, glucosamine, fructose, mannitol, sorbitol, glycine, arginine HCL, poly-hydroxy compounds, including polysaccharides such as dextran, starch, hydroxyethyl starch, cyclodextrins, N-methyl pyrollidene, cellulose and hyaluronic acid, [Carpenter et al., Develop. Biol. Standard 74:225, (1991)]. In the present formulations, the stabilizer is incorporated in a concentration of about 0.1, 0.5, 0.7, 0.8 0.9, 1.0, 1.2, 1.5, 1.7, 2, 3, 4, 5, 6, 7, 8, 9, 10, 11, 12, 13, 14, 15, 16, 17, 18, 19, 20, 30, 40, 50, 60, 70, 80, 90, 100, or 200 g/L. In one embodiment of the present invention, mannitol is used as stabilizing agent.

If desired, the formulations also include appropriate amounts of bulking and osmolarity regulating agents. Bulking agents include, for example and without limitation, mannitol, glycine, sucrose, polymers such as dextran, polyvinylpyrolidone, carboxymethylcellulose, lactose, sorbitol, trehalose, or xylitol.

Formulations and Excipients

Excipients are additives that either impart or enhance the stability and delivery of a drug product (e.g., protein). Regardless of the reason for their inclusion, excipients are an integral component of a formulation and therefore need to be safe and well tolerated by patients. For protein drugs, the choice of excipients is particularly important because they can affect both efficacy and immunogenicity of the drug. Hence, protein formulations need to be developed with appropriate selection of excipients that afford suitable stability, safety, and marketability.

The principal challenge in developing formulations for proteins is stabilizing the product against the stresses of manufacturing, shipping and storage. The role of formulation excipients is to provide stabilization against these stresses. Excipients are also be employed to reduce viscosity of high concentration protein formulations in order to enable their delivery and enhance patient convenience. In general, excipients can be classified on the basis of the mechanisms by which they stabilize proteins against various chemical and physical stresses. Some excipients are used to alleviate the effects of a specific stress or to regulate a particular susceptibility of a specific protein. Other excipients have more general effects on the physical and covalent stabilities of proteins. The excipients described herein are organized either by their chemical type or their functional role in formulations. Brief descriptions of the modes of stabilization are provided when discussing each excipient type.

The amount or range of excipient can be included in any particular formulation to achieve a biopharmaceutical formulation of the invention that promotes retention in stability of the biopharmaceutical (e.g., a protein). For example, the amount and type of a salt to be included in a biopharmaceutical formulation of the invention is selected based on the desired osmolality (i.e., isotonic, hypotonic or hypertonic) of the final solution as well as the amounts and osmolality of other components to be included in the formulation.

Further, where a particular excipient is reported in molar concentration, those skilled in the art will recognize that the equivalent percent (%) w/v (e.g., (grams of substance in a solution sample/mL of solution).times.100%) of solution is also contemplated.

The concentrations of the excipients described herein share an interdependency within a particular formulation. By way of example, the concentration of a bulking agent may be lowered where, e.g., there is a high protein concentration or where, e.g., there is a high stabilizing agent concentration. In order to maintain the isotonicity of a particular formulation in which there is no bulking agent, the concentration of a stabilizing agent would be adjusted accordingly (i.e., a "tonicifying" amount of stabilizer would be used). Excipients include, for example and without limitation, human serum albumin, mannitol, glycine, polyethylene glycol and combinations of these excipients.

Salts

Salts are often added to increase the ionic strength of the formulation, which can be important for protein solubility, physical stability, and isotonicity. Salts can affect the physical stability of proteins in a variety of ways. Ions can stabilize the native state of proteins by binding to charged residues on the protein's surface. Alternatively, salts can stabilize the denatured state by binding to peptide groups along the protein backbone (—CONH—). Salts can also stabilize the protein native conformation by shielding repulsive electrostatic interactions between residues within a protein molecule. Salts in protein formulations can also shield attractive electrostatic interactions between protein molecules that can lead to protein aggregation and insolubility. In formulations provided, the salt concentration is between about 1, 10, 20, 30, 40, 50, 80, 100, 120, 150, 200, 300, and 500 mM.

Methods of Preparation

The present invention further contemplates methods for the preparation of pharmaceutical formulations.

The present methods further comprise one or more of the following steps: adding a stabilizing agent as described herein to said mixture prior to lyophilizing, adding at least one agent selected from a bulking agent, an osmolarity regulating agent, and a excipient, each of which as described herein, to said mixture prior to lyophilization.

The standard reconstitution practice for lyophilized material is to add back a volume of pure water or sterile water for injection (WFI) (typically equivalent to the volume removed during lyophilization), although dilute solutions of antibacterial agents are sometimes used in the production of pharmaceuticals for parenteral administration [Chen, Drug Development and Industrial Pharmacy, 18:1311-1354 (1992)]. Accordingly, methods are provided for preparation of reconstituted NRG compositions comprising the step of adding a diluent to a lyophilized NRG composition of the invention.

The lyophilized material may be reconstituted as an aqueous solution. A variety of aqueous carriers, e.g., sterile water for injection, water with preservatives for multi dose use, or water with appropriate amounts of surfactants (for example, an aqueous suspension that contains the active compound in admixture with excipients suitable for the manufacture of aqueous suspensions). In various aspects, such excipients are suspending agents, for example and without limitation, sodium carboxymethylcellulose, methylcellulose, hydroxypropylmethylcellulose, sodium alginate, polyvinylpyrrolidone, gum tragacanth and gum acacia; dispersing or wetting agents are a naturally-occurring phosphatide, for example and without limitation, lecithin, or condensation products of an alkylene oxide with fatty acids, for example and without limitation, polyoxyethylene stearate, or condensation products of ethylene oxide with long chain aliphatic alcohols, for example and without limitation, heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example and without limitation, polyethylene sorbitan monooleate. In various aspects, the aqueous suspensions also contain one or more preservatives, for example and without limitation, ethyl, or n-propyl, p-hydroxybenzoate.

Administration

To administer compositions to human or test animals, in one aspect, the compositions comprises one or more pharmaceutically acceptable carriers. The phrases "pharmaceutically" or "pharmacologically" acceptable refer to molecular entities and compositions that are stable, inhibit protein degradation such as aggregation and cleavage products, and in addition do not produce allergic, or other adverse reactions when administered using routes well-known in the art, as described below. "Pharmaceutically acceptable carriers" include any and all clinically useful solvents, dispersion media, coatings, antibacterial and antifungal agents, isotonic and absorption delaying agents and the like, including those agents disclosed above.

As used herein a "resuspension solution" refers to solutions, e.g., sterile DI water or physiological saline, which can be used clinically without causing any allergic reaction or any other adverse reactions.

The pharmaceutical formulations are administered orally, topically, transdermally, parenterally, by inhalation spray, vaginally, rectally, or by intracranial injection. The term parenteral as used herein includes subcutaneous injections, intravenous, intramuscular, intracisternal injection, or infusion techniques. Administration by intravenous, intradermal, intramusclar, intramammary, intraperitoneal, intrathecal, retrobulbar, intrapulmonary injection and or surgical implantation at a particular site is contemplated as well. Generally, compositions are essentially free of pyrogens, as well as other impurities that could be harmful to the recipient.

Single or multiple administrations of the compositions are carried out with the dose levels and pattern being selected by the treating physician. For the prevention or treatment of disease, the appropriate dosage depends on the type of disease to be treated, as defined above, the severity and course of the disease, whether drug is administered for preventive or therapeutic purposes, previous therapy, the patient's clinical history and response to the drug, and the discretion of the attending physician.

Kits

As an additional aspect, the invention includes kits which comprise one or more lyophilized compositions packaged in a manner which facilitates their use for administration to subjects. In one embodiment, such a kit includes pharmaceutical formulation described herein (e.g., a composition comprising a therapeutic protein or peptide), packaged in a container such as a sealed bottle or vessel, with a label affixed to the container or included in the package that describes use of the compound or composition in practicing the method. In one embodiment, the kit contains a first container having a therapeutic protein or peptide composition and a second container having a physiologically acceptable reconstitution solution for the composition. In one aspect, the pharmaceutical formulation is packaged in a unit dosage form. The kit may further include a device suitable for administering the pharmaceutical formulation according to a specific route of administration. Preferably, the kit contains a label that describes use of the pharmaceutical formulations.

Dosages

The dosage regimen involved in a method for treating a condition described herein will be determined by the attending physician, considering various factors which modify the action of drugs, e.g. the age, condition, body weight, sex and diet of the patient, the severity of any infection, time of administration and other clinical factors.

Unless defined otherwise, all technical and scientific terms used herein have the same meaning as is commonly understood by one of ordinary skill in the art to which this invention belongs. If a definition set forth in this section is contrary to or otherwise inconsistent with a definition set forth in the patents, applications, published applications and other publications that are herein incorporated by reference, the definition set forth in this section prevails over the definition that is incorporated herein by reference.

From the foregoing description, it will be apparent that variations and modifications can be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

The following examples are provided by way of illustration, not limitation.

Examples

The invention is illustrated by the following examples which are not intended to be limiting in any way. As used herein, "rhNRG-1" used in the examples refers to proteins or peptides which consist of amino acid sequence of SEQ ID NO: 2

Example 1: PH-Stability Profiling for rhNRG-1

1. Objectives of the Experiment 1.1 To Generate a pH-Stability Profile of rhNRG-1 in Various pH Buffers (pH 3 to pH 10) by SDS-PAGE
1.2 To Generate a pH-Stability Profile of rhNRG-1 in Various pH Buffers (pH 3 to pH 8) and DI-Water by RP-HPLC
1.3 Based on Findings from Objectives 1.2, Generate a pH Stability Profile for a Narrow Working pH Range (pH 2.3 to 4.3)
1.4 Based on the Narrow pH Stability Study, Determine the Optimal pH for an rhNRG-1 Formulation 2. Experimental Procedure 2.1 Develop a RP-HPLC Method to Determine the Purity of rhNRG-1 Drug Substance.

TABLE 1 the method conditions

| | |
|---|---|
| HPLC System | Agilent 1050 |
| Column | Phenomenex Jupiter, 5 µm 4.6 × 250 mm, 5 µm, 300 Å (PN 00G-4167-EO) |
| Mobile Phase (MP) | MP A: 0.1% TFA in acetonitrile and MP B: 0.1% TFA in water (both MP 0.45 µm filtered and degassed) |

| Gradient | Time (minutes) | % MP A | % MP B |
|---|---|---|---|
| | 0 | 0 | 100 |
| | 10 | 20 | 80 |
| | 40 | 32 | 68 |
| | 45 | 100 | 0 |
| | 50 | 0 | 100 |
| | 60 | 0 | 100 |

| | |
|---|---|
| Flow Rate | 1.0 mL/min |
| Detection Wavelength | Ultraviolet (UV): 214 nm |
| Column Temperature | 30° C. |
| Sample Temperature | 5° C. |
| Injection Volume | 80 µL |
| Run Time | 60 min |
| HPLC Standard and Sample Diluent ("Diluent") | DI water |

RhNRG-1, batch 201204001, which contains 1.24 mg/mL rhNRG-1, 20 mM phosphate buffer and 0.5M NaCl, pH 5.5 ("API") was used for the preparation of standard solution for all HPLC analysis.

Representative chromatograms of the rhNRG-1 Diluent and standard solution prepared at 0.25 mg/mL in the Diluent are showed in FIG. 1 (upper and lower respectively).

TABLE 2

Method Precision evaluated by injecting the standard at 0.25 mg/mL six times

| STD 0.25 mg/mL | Peak Area |
|---|---|
| Inj #1 | 9929 |
| Inj #2 | 9901 |
| Inj #3 | 9819 |
| Inj #4 | 9924 |
| Inj #5 | 9781 |
| Inj #6 | 9663 |
| Average | 9874 |
| RSD* | 0.4 |

*The RSD for the peak areas generated was 0.4. This is within the precision acceptable criteria of <2.0.

2.2 Prepare the Buffers Form pH 3 to pH 10

In a 15 mL plastic tube, add the API and DI-water or a New Buffer. Mix into a solution containing 0.25 mg/mL rhNRG-1, 10 mM New Buffer, 4 mM phosphate (from the API) and 0.1 M NaCl (from the API).

TABLE 3 the final pH and the New Buffer

| pH (initial) | New Buffer |
|---|---|
| 3.19 | Sodium phosphate |
| 4.17 | Sodium acetate |
| 5.08 | Sodium acetate |
| 5.47 | Histidine |
| 6.02 | Sodium citrate |
| 7.00 | Sodium phosphate |
| 8.07 | Sodium bicarbonate |
| 9.02 | Glycine and diluted Sodium hydroxy |
| 10.05 | Glycine and diluted Sodium hydroxy |
| 5.63 | No New Buffer added, pH not adjusted |

TABLE 4 the situation of each solution sealed in glass vials and stored

| Storage temperature | # of Vials |
|---|---|
| 2-8° C. | 2 |
| 40° C. | 3 |
| 60° C. | 3 |

2.3 Detect the Purity by SDS-PAGE

For 40° C., test by SDS-PAGE after 10 days. Destain I (45% water, 45% methanol, 10% acetic acid, freshly made); 0.1% Coomasic Blue stain; The running gel (12%-15%) serves to separate individual polypeptides into discrete bands.

2.4 Detect the Solution by RP-HPLC

For 60° C., remove 150 µL and test by HPLC after 0, 7.5, 24, 48, 65 and 77 hr.

For 40° C., remove 150 µL and test by HPLC after 28.5, 49 and 77 hr.

Preparation for narrow pH study (pH 2.3 to 4.3):

In a plastic tube, add the API and DI-water. Mix into a solution containing 0.25 mg/mL rhNRG-1, 4 mM phosphate (from the API) and 0.1M NaCl (from the API). Adjust pH down using a diluted HCl. Once the first target is reached, transfer about 8 mL into a separate plastic tube and continue the titration to hit the next target and collect about 8 mL at each target (i.e. 4.29, 3.90, 3.78, 3.47, 3.36, 3.17, 3.02, 2.85, 2.58, 2.37 and 2.33). For each pH, transfer into glass vials for total 5 vials each level. Place one vial each at 2-8, 25, 40, 50 and 60° C.

For 60° C., remove 200 μL and test by HPLC after 0, 3.7, 4.7 and 5.7 days

For 50° C., remove 200 μL and test by HPLC after 0, 4.7 and 11 days

For 40° C., remove 200 μL and test by HPLC after 0, 5.7, 7 and 11 days

Construct a narrow range pH-rate (stability) profile at each temperature.

Derive an Arrhenius equation and predict shelf life at 5° C.

3. Results and Conclusions

Figure 2:
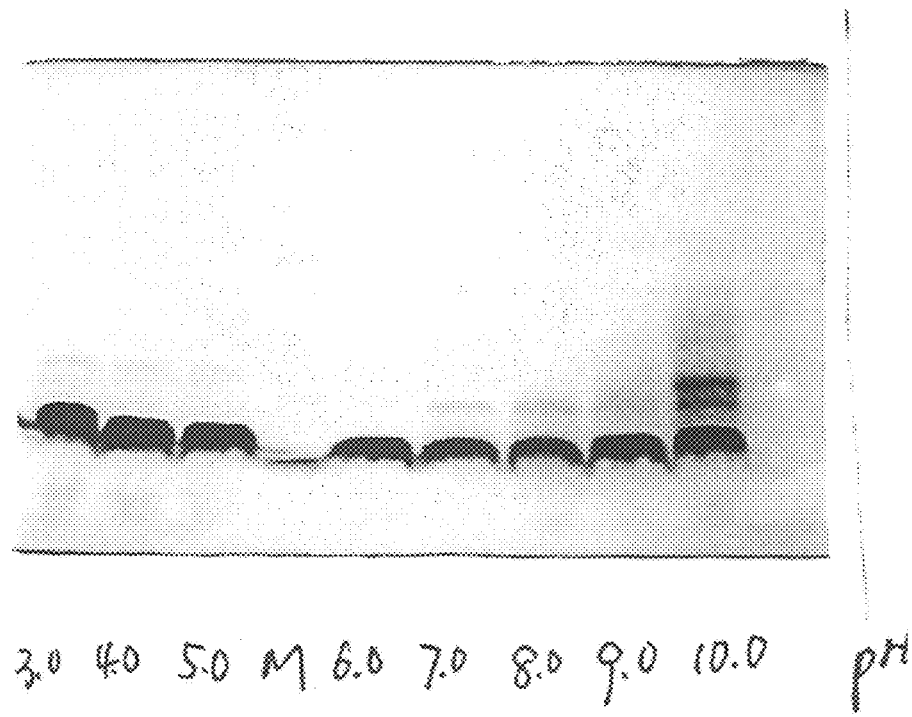
FIG. 2: Representative SDS-PAGE chromatogram for pH 3 to 10

Representative SDS-PAGE chromatograms for pH 3 to 10 are shown in FIG. 2.

The initial concentration and post-stress concentration of rhNRG-1 as measured by the RP-HPLC method are listed below:

TABLE 5 results for pH 3 to 8 at 40° C.

| pH | Initial Conc (mg/mL) | 28.5 hr (% over initial conc.) | 49 hr (% over initial conc.) | 77 hr (% over initial conc.) |
|---|---|---|---|---|
| 3.19 | 0.241 | 97 | 97 | 96 |
| 4.17 | 0.247 | 97 | 97 | 93 |
| 5.08 | 0.242 | 94 | 94 | 86 |
| 6.02 | 0.251 | 94 | 94 | 86 |
| 7.00 | 0.251 | 92 | 87 | 82 |
| 8.07 | 0.253 | 89 | 83 | 68 |
| 5.63 | 0.251 | 92 | 91 | 38 |

TABLE 6 results for pH 3 to 8 at 60° C.

| pH | Initial Conc (mg/mL) | 7.5 hr (% over initial conc.) | 24 hr (% over initial conc.) | 48 hr (% over initial conc.) | 65 hr (% over initial conc.) | 77 hr (% over initial conc.) |
|---|---|---|---|---|---|---|
| 3.19 | 0.241 | 98 | 93 | 89 | 82 | 72 |
| 4.17 | 0.247 | 99 | 93 | 91 | 84 | 78 |
| 5.08 | 0.242 | 98 | 92 | 93 | 82 | 82 |
| 5.47 | 0.248 | 95 | 92 | 86 | 79 | 79 |
| 6.02 | 0.251 | 95 | 88 | 85 | 72 | 72 |
| 7.00 | 0.251 | 90 | 76 | 65 | NT | NT |
| 8.07 | 0.253 | 68 | 4 | NT | NT | NT |
| 5.63 | 0.251 | 95 | 84 | 82 | 69 | 64 |

NT: Not Tested.

TABLE 7 results for pH 2.3 to 4.3 at 40° C.

| pH | Initial Conc (mg/mL) | 5.7 days (% over initial conc.) | 7 days (% over initial conc.) | 11 days (% over initial conc.) |
|---|---|---|---|---|
| 4.29 | 0.235 | All chromatograms for pH 3.8 at 40° C. showed peaks that co-eluted; it was not possible to integrate the individual peaks | | |
| 3.90 | 0.230 | 101 | 96 | 88 |
| 3.36 | 0.230 | 101 | 97 | 90 |
| 3.02 | 0.236 | 99 | 94 | 88 |
| 2.58 | 0.238 | 96 | 89 | 83 |
| 2.37 | 0.241 | 90 | 83 | 77 |

TABLE 8 results for pH 2.3 to 4.3 at 50° C.

| pH | Initial Conc (mg/mL) | 5.7 days (% over initial conc.) | 7 days (% over initial conc.) | 11 days (% over initial conc.) |
|---|---|---|---|---|
| 4.29 | 0.235 | 100 | NA | 78 |
| 3.90 | 0.230 | 102 | 88 | 79 |
| 3.36 | 0.230 | 99 | 85 | 76 |
| 3.02 | 0.236 | 95 | 79 | 70 |
| 2.58 | 0.238 | 90 | 54 | 35 |
| 2.37 | 0.241 | 82 | 53 | 36 |

NA: Not available

TABLE 9 results for pH 2.3 to 4.3 at 60° C.

| pH | Initial Conc (mg/mL) | 3.7 days (% over initial conc.) | 4.7 days (% over initial conc.) | 5.7 days (% over initial conc.) |
|---|---|---|---|---|
| 4.29 | 0.235 | 80 | NA | 72 |
| 3.90 | 0.230 | 83 | 81 | 73 |
| 3.36 | 0.230 | 77 | 69 | 63 |
| 3.02 | 0.236 | 70 | 68 | 0 |
| 2.58 | 0.238 | 62 | 60 | 55 |
| 2.37 | 0.241 | 55 | 57 | 43 |

NA: Not available

Figure 3:
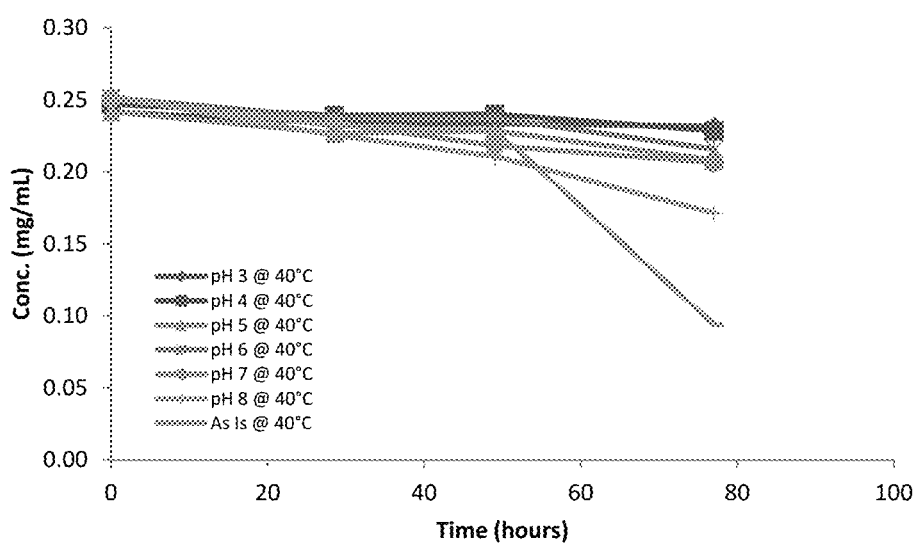
FIG. 3: The results of conc-vs-time profiles at pH 3 to 8 at 40° C.

Conc-vs-time profiles at pH 3 to 8 at 40° C. are shown in FIG. 3.

Figure 4:
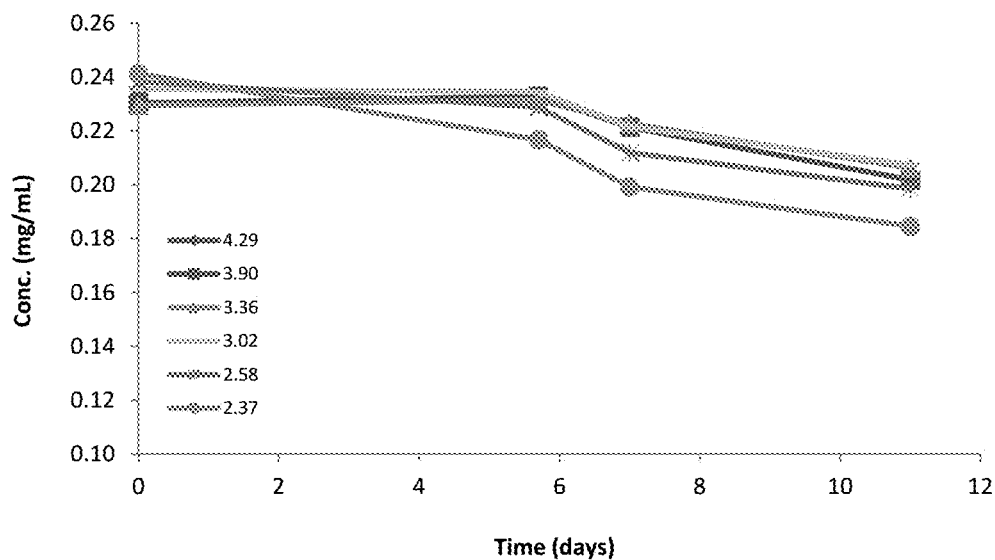
FIG. 4: The results of conc-vs-time profiles at pH 2.3 to 4.3 at 40° C.

Conc-vs-time profiles at pH 2.3 to 4.3 at 40° C. are shown in FIG. 4.

Figure 5:
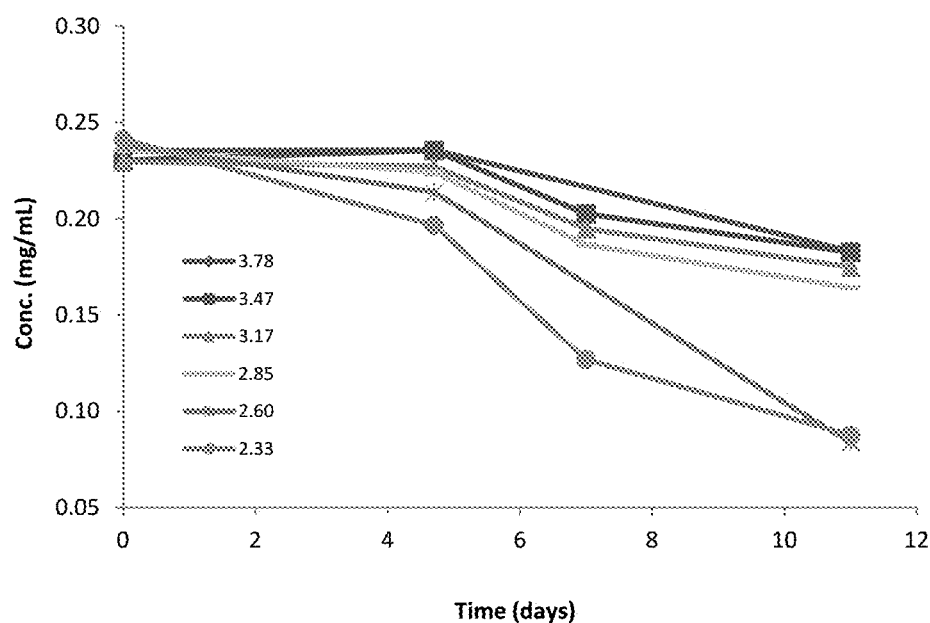
FIG. 5: The results of conc-vs-time profiles at pH 2.3 to 4.3 at 50° C.

Conc-vs-time profiles at pH 2.3 to 4.3 at 50° C. are shown in FIG. 5.

Figure 6:
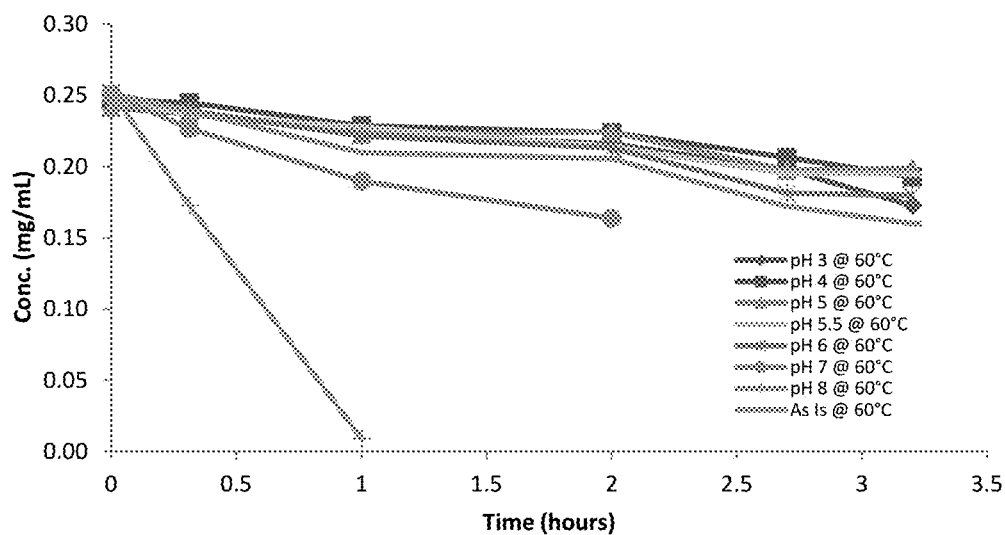
FIG. 6: The results of conc-vs-time profiles for pH 3 to 8 at 60° C.

Conc-vs-time profiles for pH 3 to 8 at 60° C. are shown in FIG. 6.

Figure 7:
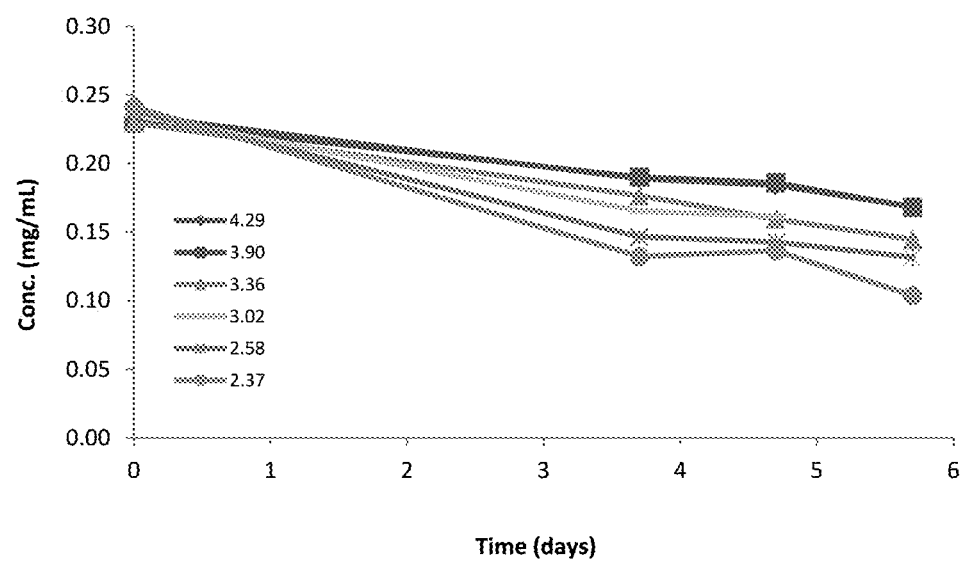
FIG. 7: The results of conc-vs-time profiles at pH 2.3 to 4.3 stored at 60° C.

Conc-vs-time profiles at pH 2.3 to 4.3 stored at 60° C. are shown in FIG. 7.

For each Conc-vs-time profile, a linear regression analysis was performed and the slope of the regression equation was used to represent the rate of degradation in mg/mL/hr assuming zero order kinetics.

Figure 8:
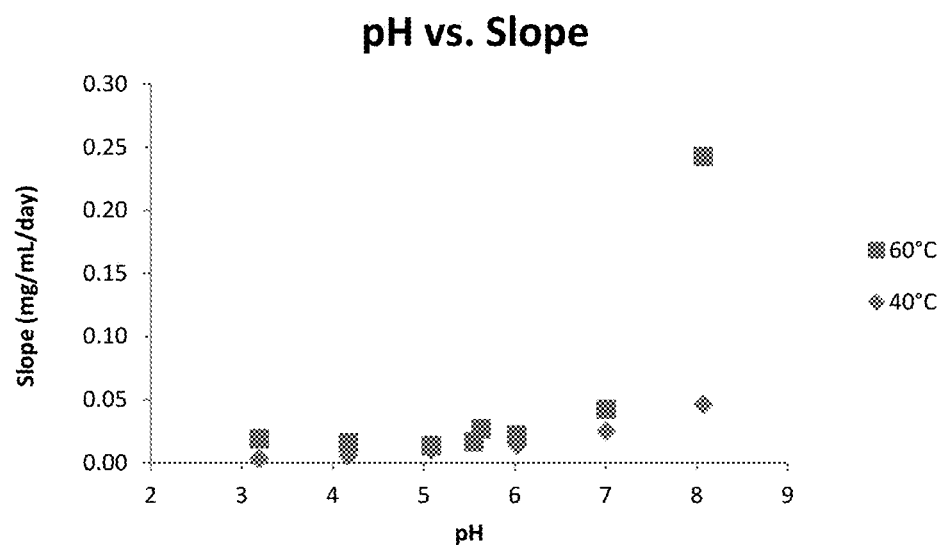
FIG. 8: The results of pH-vs-degradtion rate (slope) profiles for pH 3 to 8

PH-vs-degradtion rate (slope) profiles for pH 3 to 8 are shown in FIG. 8.

Figure 9:
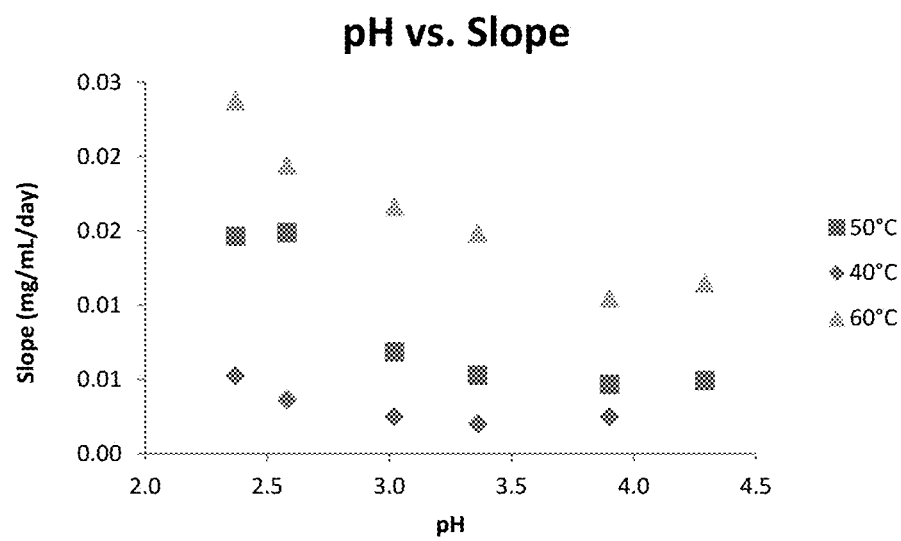
FIG. 9: The results of pH-vs-degradtion rate (slope) profiles for pH 2.3 to 4.3

PH-vs-degradtion rate (slope) profiles for pH 2.3 to 4.3 are shown in FIG. 9.

Figure 10:
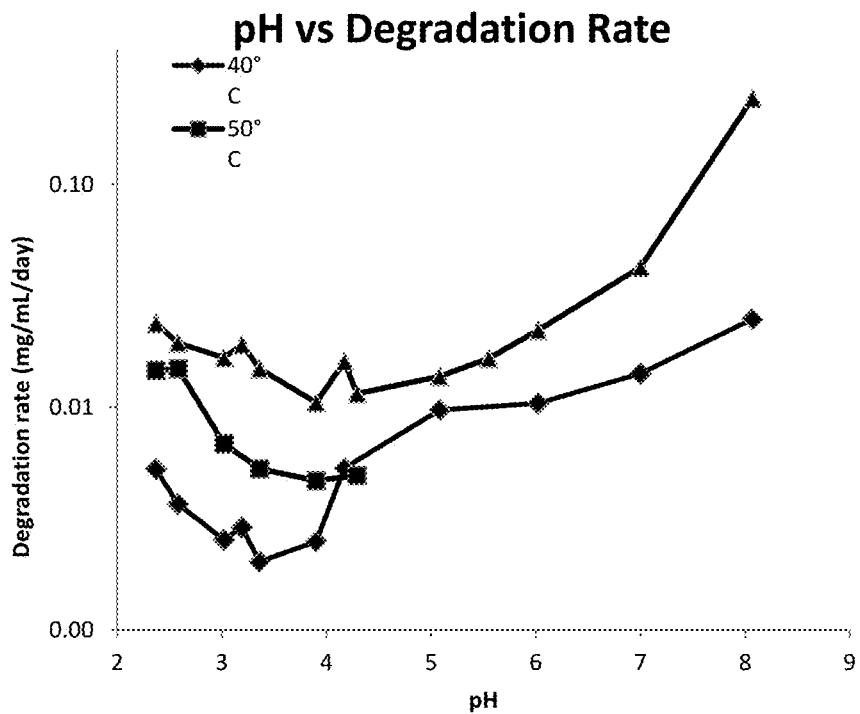
FIG. 10: The results of pH-vs-degradtion rate (slope) profiles for pH ranging from 2.3 to 8

PH-vs-degradtion rate (slope) profiles for pH ranging from 2.3 to 8 are shown in FIG. 10.

At each pH (3 to 8) and temperature, the estimated degradation rate and T90 (time to degrade 10% of the initial concentration or 0.025 mg/mL) are provided as follow (Table 10):

| | 40° C. | | 60° C. | |
|---|---|---|---|---|
| pH | Rate of degradation (mg/mL/hr) | T90 (day) | Rate of degradation (mg/mL/hr) | T90 (day) |
| 3.19 | 0.0001 | 10.4 | 0.0006 | 1.7 |
| 4.17 | 0.0002 | 5.2 | 0.0006 | 1.7 |
| 5.08 | 0.0004 | 2.6 | 0.0006 | 1.7 |
| 5.47 | — | — | 0.0007 | 1.5 |
| 6.02 | 0.0004 | 2.6 | 0.0009 | 1.2 |
| 7.00 | 0.0006 | 1.7 | 0.0015 | 0.7 |
| 8.07 | 0.001 | 1.0 | 0.0061 | 0.2 |
| 5.63 | 0.0019 | 0.5 | 0.001 | 1.0 |

Using the 40, 50 and 60° C. data for each pH (2.3 to 3.9), an Arrhenius plot was used to predict the shelf life at 5° C. for each pH level. The T90 values calculated from the Arrhenius plots are provided as follows (Table 11):

| pH | T90 (days) | T90 (months) |
|---|---|---|
| 2.37 | 166 | 6 |
| 2.58 | 317 | 11 |
| 3.02 | 612 | 70 |
| 3.36 | 1092 | 36 |
| 3.90 | 239 | 8 |

Figure 11:
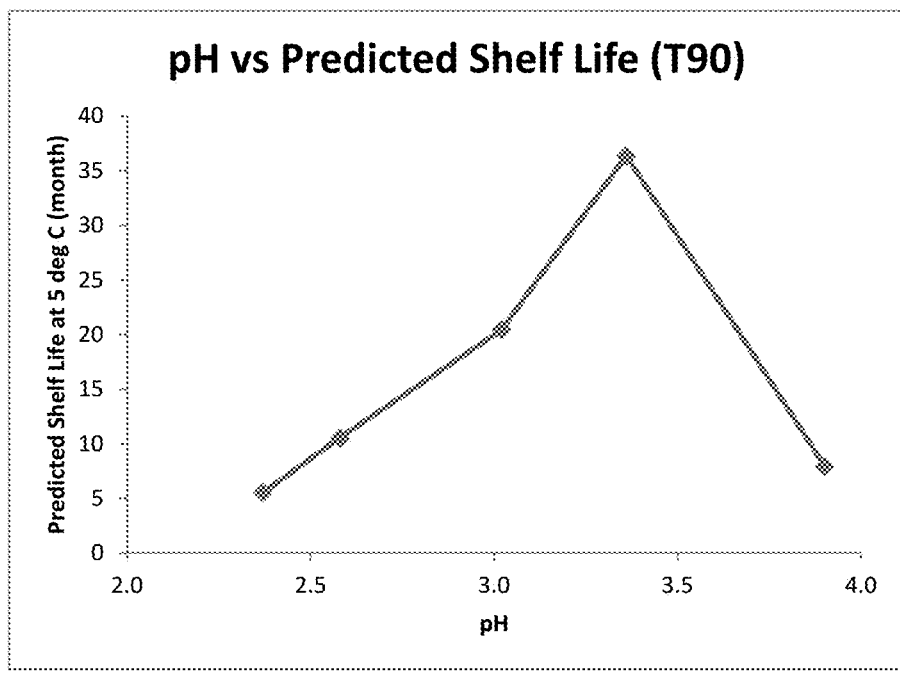
FIG. 11: A graphical representation of the pH versus predicted shelf life T(90)

FIG. 11 is a graphical representation of the pH versus predicted shelf life T(90).

Figure 12:
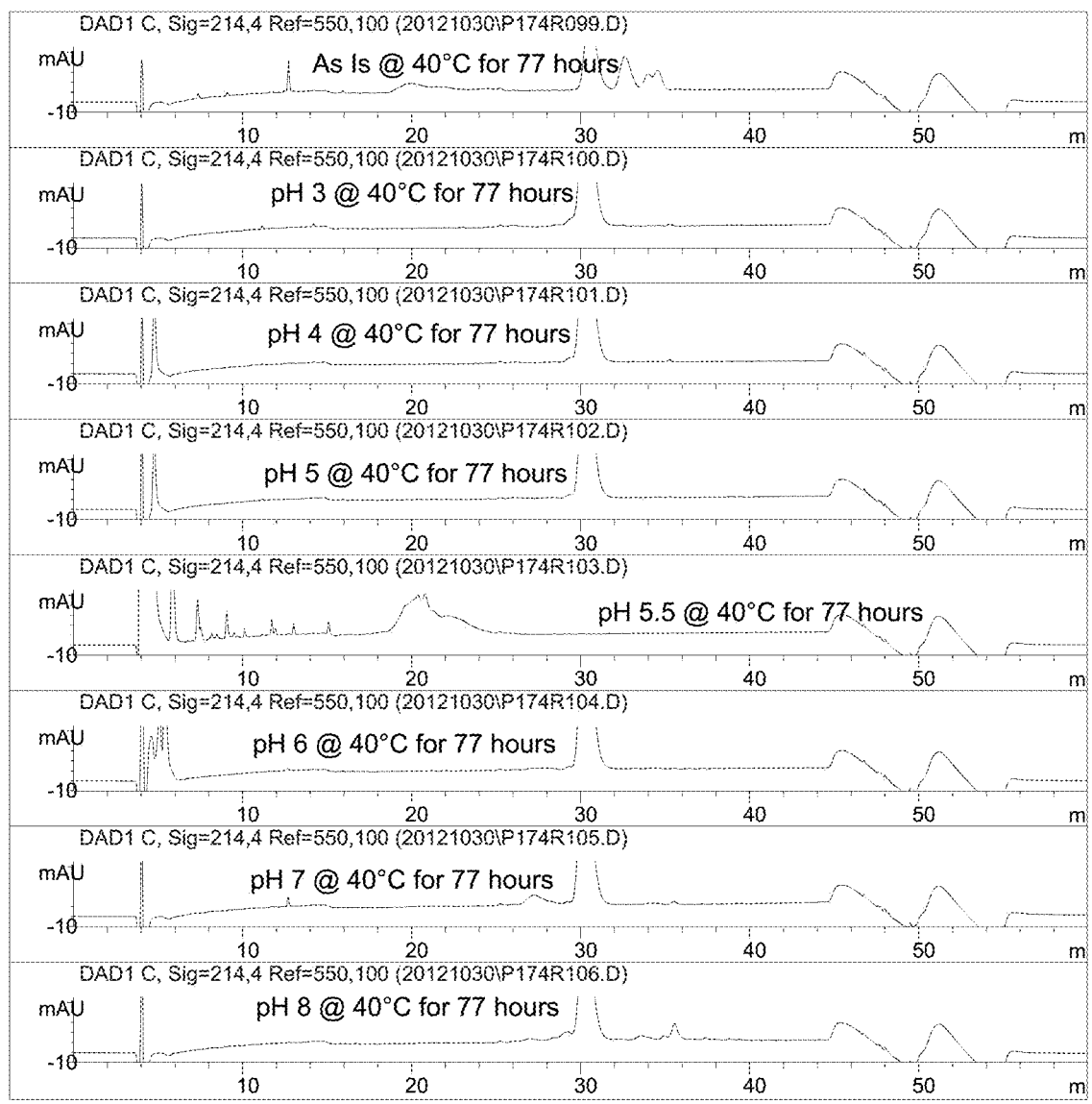
FIG. 12: Representative chromatograms for pH 3 to 8 stored at 40° C. for 77 hours.

Chromatograms for pH 3 to 8 stored at 40° C. for 77 hours are shown in FIG. 12.

Figure 13:
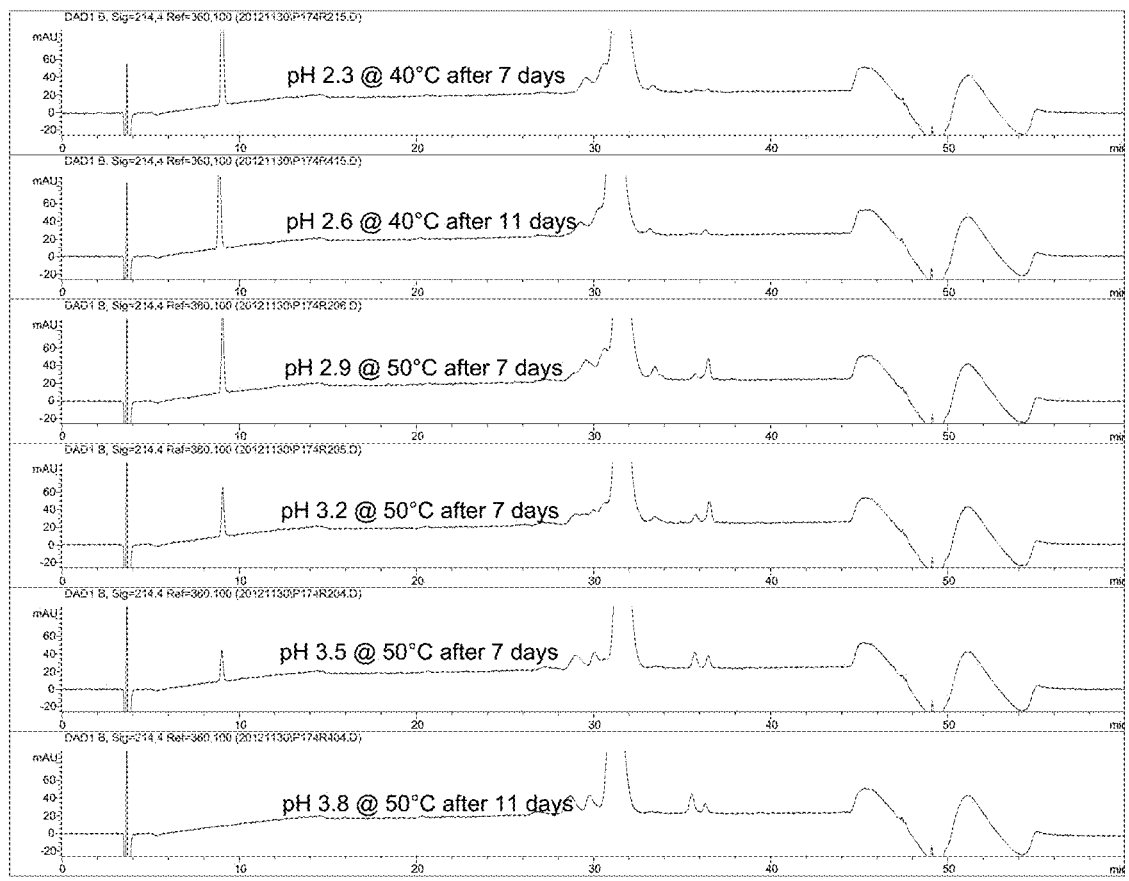
FIG. 13: Representative chromatograms for pH 2.3 to 3.8.

Chromatograms for pH 2.3 to 3.8 are shown in FIG. 13.

Conclusions:
1. rhNRG-1 stability in solution is highly pH dependent, the rhNRG-1 is more stable in acid solution (PH 3.0 to 7.0) than in basic solution (PH 8.0 to 10.0)
2. The best stability observed of the rhNRG-1 is at the lowest pH (3.2).
3. At the lower pH, the T90 is about 2× as the one at pH 4.2 or about 20× as the one in its original buffer (pH 5.5, as is). Therefore, one may expect a great improvement in stability by adapting a lower pH for a rhNRG-1 solution.
4. The narrow pH study demonstrated the best stability at pH 3.4 (±0.2).

Example 2: Forced Degradation Study

1. Objective of the Experiment

To study the stability of rhNRG-1

2. Experimental Procedure

The API solution was forced to degrade as follow (Table 12):

| Condition | Preparation |
|---|---|
| Oxidation | 1:1:3 (v/v/v) mixture of 1.24 mg/mL API Solution with 0.3% $H_2O_2$ and DI water (final $H_2O_2$ is 0.06%) stored at RT for about 0.3, 2, 4 and 7 hours |
| Day light | 1.24 mg/mL API Solution diluted 5X with DI water exposed to direct sunlight at RT for about 1 and 4 days |

The samples collected at time point was analyzed by the RP-HPLC.

3. Results and Conclusions

TABLE 13 results of oxidation exposure

| Oxidation Exposure | rhNRG-1 conc. (mg/mL) |
|---|---|
| 0.3 hours | 0.24 |
| 2.4 hours | 0.15 |
| 4.5 hours | 0.10 |
| 7.1 hours | 0.07 |

Figure 14:
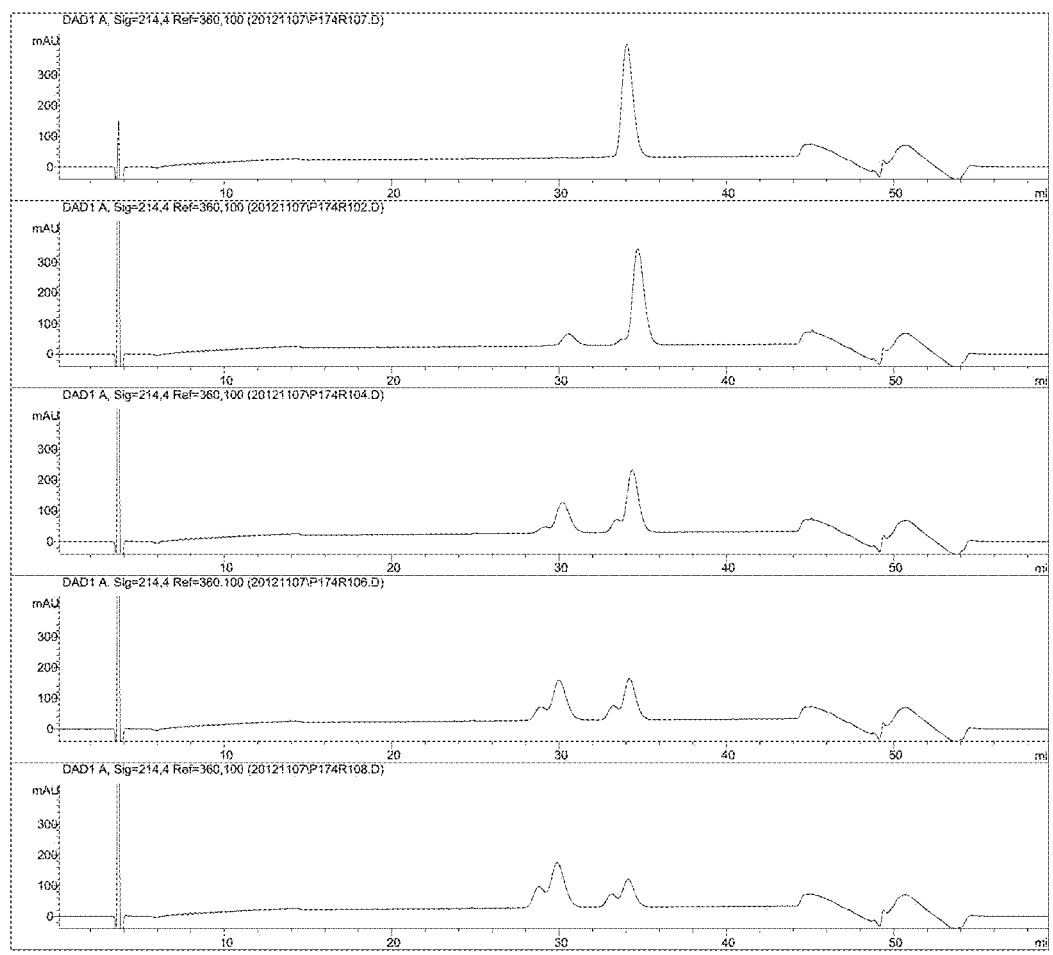
FIG. 14: Representative chromatograms of the stressed solutions (From top down: Standard 0.255 mg/mL, $H_2O_2$ after 20 minutes, $H_2O_2$ after 2 hours and 25 minutes, $H_2O_2$ after 4 hours and 30 minutes, $H_2O_2$ after 7 hours and 7 minutes).

Representative chromatograms of the stressed solutions are shown in FIG. 14 (From top down: Standard 0.255 mg/mL, $H_2O_2$ after 20 minutes, $H_2O_2$ after 2 hours and 25 minutes, $H_2O_2$ after 4 hours and 30 minutes, $H_2O_2$ after 7 hours and 7 minutes)

Conclusions:
1. rhNRG-1 is very sensitive to peroxide and prone to oxidation.
2. Antioxidants and stabilizer agents should be considered to use in the formulation for stability enhancement.

Example 3: The Effect of Different Excipients on the Stability of rhNRG-1 Formulations 1. Objective of the Experiment To study the effect of different excipients on the stability of rhNRG-1 formulations 2. Experiment Material 2.1 Sixteen rhNRG-1 Formulations were Listed in Table 14

2.2 SHELLAB/Model1535 Thermostated Container (Sheldon Company)

2.3 HPLC Angilent 1200 (Angilent Company)

2.4 Gel Column ZORBAX GF-250 (4.6 mm×250 mm)

TABLE 14

Listing of test formulations

| Excipients | Concentration (%) | Sample Name | Added amount (µl) | rhNRG-1 (µl) | 10 mM PH6.0 PB (µl) | Sterile water (µl) |
|---|---|---|---|---|---|---|
| Lactose | 0.5 | A1 | 25 | 200 | 50 | 725 |
| (20%) | 5 | A2 | 250 | | | 500 |
| Trehalose | 0.5 | B1 | 12.5 | | | 737.5 |
| (40%) | 8 | B2 | 200 | | | 550 |
| Glucan | 0.2 | C1 | 50 | | | 700 |
| (4%) | 2 | C2 | 500 | | | 250 |
| PVP | 0.5 | D1 | 50 | | | 700 |
| (10%) | 5 | D2 | 500 | | | 250 |
| Arginine | 50 mM | E1 | 50 | | | 700 |
| (1M) | 400 mM | E2 | 400 | | | 350 |
| Sucrose | 0.5 | F1 | 10 | | | 740 |
| (50%) | 10 | F2 | 200 | | | 550 |
| Mannitol | 0.5 | G1 | 25 | | | 725 |
| (20%) | 5 | G2 | 250 | | | 500 |
| Glycine | 0.1M | H1 | 50 | | | 700 |
| (2M) | 1M | H2 | 500 | | | 250 |

3. Experimental Procedure 3.1 The Samples were Stayed Under 37° C. for 5 Days 3.2 Test the Sample Purity by SEC-SCPLC Mobile phase: 0.7 M NaCl, 30 mM PB (pH7.0)

HPLC chromatographic condition: flow speed 0.5 ml/min, injected amount 20 µl, determined wave length 450 nm, record time 20 min.

4. Results

Analysis was carried out with area normalization method calculate the purity of each sample. The test results of the four rhNRG-1 formulations are listed in Table 15.

TABLE 15

Purity of test formulations after 5 days

| Stabilizer or Bulking agent | Sample name | SEC-HPLC Purity (%) |
|---|---|---|
| Lactose | A1 | 99.41 |
|  | A2 | 96.79 |
| Trehalose | B1 | 99.37 |
|  | B2 | 98.00 |
| Glucan | C1 | 99.33 |
|  | C2 | 85.75 |
| PVP | D1 | No data |
|  | D2 | No data |
| Arginine | E1 | 98.22 |
|  | E2 | 91.64 |
| Sucrose | F1 | 98.70 |
|  | F2 | 62.20 |
| Mannitol | G1 | 98.70 |
|  | G1 | 98.13 |
| Glycine | H1 | 98.55 |
|  | H2 | 98.63 |

The purity data of Glucan formulations (C1&C2), Arginine formulations (E1&E2) and Sucrose formulations (F1&F2) are not concordant. So glucan, arginine and sucrose are not good excipients for the rhNRG-1 formulations. PVP (polyvinylpyrolidone) is a bulking agent and rhNRG-1 formulations with it fail to provide the purity data by SEC-HPLC. The results showed lactose, trehalose, mannitol and glycine are preferred excipients for the rhNRG-1 formulations.

Example 4: The Effect of Human Serum Albumin (HSA) Concentration on the Biological Activity of NRG Formulations 1. Abstract HER2/neu gene encods a trans-membrane protein p185, which is a tyrosine protein kinase. Binding of Neuregulin-1 with ErbB3 or ErbB4 induces heterodimer ErbB3-ErbB2 and ErbB4-ErbB2 formation and activates HER2 encoded tyrosine protein kinase, mediating the transmission of functioning signal of Neuregulin-1. Based on the fact that binding of Neuregulin-1 with its receptors triggers phosphorylation of ErbB2 protein, a rapid, sensitive and high flux method was established for in vitro quantitatively determining biological activity of Recombinant Neuregulin-1.

2. Objective of the Experiment

To study the effect of different concentrations of HSA on the biological activity of NRG formulations 3. Experiment Material 3.1 rhNRG-1 Formulations
Reference Sample: 0 g/L HSA, 250 µg/L rhNRG-1, 10 mM phosphate buffering reagent, 150 mM NaCl, 50 g/L mannitol
Test sample A: 0.5 g/L HSA, 250 µg/L rhNRG-1, 10 mM phosphate buffering reagent, 150 mM NaCl, 50 g/L mannitol
Test sample B: 2 g/L HSA, 250 µg/L rhNRG-1, 10 mM phosphate buffering reagent, 150 mM NaCl, 50 g/L mannitol
Test sample C: 8 g/L HSA, 250 µg/L rhNRG-1, 10 mM phosphate buffering reagent, 150 mM NaCl, 50 g/L mannitol
3.2 96 Holes Cell Cultural Plate (Corning Company); Costar 96 Holes ELISA Detecting Plate.
3.3 Human Breast Cancer Cell Strain, Introduced from the U.S. ATCC, was Cultivated in Base Cultural Medium Under 37° C. and 50% $CO_2$.
3.4 Weighing a Given Amount of DMEM, Quantifying to Corresponding Volume, Added 3.7 g/L of $NaHCO_2$, 0.1 g/L Glutamine and 5.5 g/L of HEPES.
3.5 Base Culture Medium DMEM Culture Medium with 10% Fetal Calf Serum and Insulin 9 mg/L, Stored at 4° C.
3.6 Sterilized PBS (0.01M, pH 7.4).
3.7 0.25% Pancreatic Enzyme Preparing with $Ca^{2+}$ and $Mg^{2+}$ Free PBS.
3.8 Anti-ErbB2 Monoclonal Antibody Coating Buffer Solution, Lotion. Select Mouse Anti-Human ErbB2 Extra-Cell Functioning Domain H4 Monoclonal Antibody with No Cross Reaction with ErbB3 and ErbB4. Coating Buffer Solution; pH 9.6, 0.05M Carbonate Buffer Solution. Lotion: 0.01M PBS+0.05% Tween-20.
3.9 Horse-Radish Peroxidase (HRP) Labeled Mouse Anti-Human Phosphorylated Protease Monoclonal Antibody (Anti-P-Tyr-HRP)
3.10 Substrate, Substrate Buffer Solution Substrate (TMB): 2 mg/ml TMB (Prepare with Absolute Alcohol). Substrate Buffer: 0.2M Citric Acid+0.1M $Na_2HPO_4$ (pH 5.0). Operating Substrate: Substrate Buffer Solution 9 ml+TMB 1 ml+3% $H_2O_2$ 10 Ul (Prepared as Needed).
3.11 Termination Agent 2N $H_2SO_4$.
3.12 Cell Defragmentation Solution 150 mM NaCl+50 mM Hepes+1% Triton-X 100+2 mM (Sodium Orthovanadate)+0.01% (Thimerosol). One Tablet of Mixed Protease Inhibitor (Tabletten, Proteasen-Irhibitoren-Cocktail) is Added into Every 25 ml Prior to the Operation.

4. Experimental Procedure 4.1 The Samples were Stayed Under 37° C. for 4 Days
4.2 Inoculation of Cells
MCF-7 cells were amplified to a given amount, washed with sterilized PBS solution, then digested with 0.25% trypsinase. After counting, the concentration of cells was regulated with base culture medium. The cells were added into 96 holes cell culture plate, $5 \times 10^4$/hole, 100 µl/hole, and cultured overnight in the culture box under 37° C. and 5% $CO_2$.
4.3 Cell Starvation
Suck up all the culture medium in the 96 holes plate, wash each hole with 37° C. warmed PBS, then add 100 µl DMEM culture medium (calf serum free and without insulin). Cells were cultured for 24 hours in the culture box under 37° C. and 5% $CO_2$.
4.4 Coating
Dilute the anit-ErbB2 extra-cell functioning domain H4 antibody with coating buffer solution to be 6 µg/ml, then add 50 µl per hole to the 96 holes ELISA plate, set over night (16-18 hours) under 4° C.
4.5 Dilute Control Solution and Sample Solution Expected to be Tested
Dilute control solution and sample expected to be tested with DMEM culture medium respectively (calf serum free and without insulin) to be 2 µg/ml, then again carry out 3 times gradient dilution with a total of 9 dilution.
4.6 Phosphorylation of the Cells
Suck up the post-starvation 96 holes cell culture medium, add standard material and sample expected to be tested, 100·mu·l per hole, set up 2 double hole for each concentration. Set up negative control at the same time (i.e. DMEM culture medium placebo control). Reaction for 20 minutes under 37° C.

4.7 Decomposition of the Cells

Rapidly suck out the sample and wash once with PBS, 100 μl of fragmentation solution was added into each hole, fragmenting for 30 minutes in 4° C. refrigerator. Horizontally agitate under ice-bath condition till all the anchorage-dependent cell drop down, 4° C., 15,000 rpm centrifuge for 15 minutes.

4.8 Sealing the ELISA Detecting Plate

Wash the plate 5 times. Prepare 5% skimmed milk with wash solution, add 200 μl to each hole of the plate, set under 37° C. for 2 hours.

4.9 Add Sample

After wash 3 times the sealed ELISA plate, add standard cell fragmentation solution and testing sample fragmentation solution with 90 μl per hole, set up negative control at the same time, set for 1 hour under 37° C.

4.10 Add Enzyme Labeled Antibody

Wash the plate 5 times, dilute HRP enzyme linked mouse anti-phosphorylated tyrosine protein antibody with 1:500 lotion (determined by the product using guide and the using time), add 100 μl into each hole of the plate. Set for 1 hour under 37° C.

4.11 Color Development of the Substrate

Wash the plate 5 times, prepared substrate working solution was added into with 100 μl per hole, set for 10 minutes under 37° C.

4.12 Termination

2N $H_2SO_4$ was added into with 50 μl per hole to terminate the reaction.

4.13 OD Value Reading

Colorimetric analysis on the ELISA reader, determine wave length of 450 nm, reference wave length of 655 nm, record the results.

5. Results

Construction with concentration of Recombinant Human Neuregulin-1 versus OD value and analysis was carried out with linear regression method calculate the half effective dosage of each sample expected for testing. The test results of the four rhNRG-1 formulations are listed in Table 16.

TABLE 16

Biological activity of test samples

| Sample | $OD_{50}$ value | $EC_{50}$ value | Standard sample $EC_{50}$ / sample $EC_{50}$ | specific activity ($\times 10^4$ U/mg) | Biological activity ($\times 10^4$ U) |
|---|---|---|---|---|---|
| Reference Sample | 0.391 | 0.0505 | — | 0.60 | 0.150 |
| Sample A | 0.393 | 0.0439 | 1.15 | 0.69 | 0.173 |
| Sample B | 0.406 | 0.0217 | 2.33 | 1.40 | 0.35 |
| Sample C | 0.424 | 0.0189 | 2.67 | 1.60 | 0.40 |

The biological activity data of sample B and sample C (See in table 16) is obviously better than the data of reference sample and the sample A. The results indicated the concentration of HSA at 2 g/L (sample B) or at 8 g/L (sample C) are preferred concentrations for the rhNRG-1 formulations.

Example 5: Accelerated and Long-Term Stability Testing

1. Objectives of the Experiment

To study the stability of rhNRG-1 final drug products

2. Experimental Procedure

Experiment Material: four rhNRG-1 final drug product (FDP) batchs that have been manufactured by Zensun. The rhNRG-1 FDP was obtained by lyophilizing the solution containing about 250 μg/L rhNRG-1, about 10 mM phosphate buffer at about pH 6.0, about 50 g/L mannitol, about 2 g/L HSA and about 150 mM NaCl. After lyophilization, the amount of the product in each vial is about 60 mg.

Studies were conducted to evaluate the stability of the rhNRG-1 final drug product (FDP) stored at both the recommended and elevated storage conditions, can be found in Table 17. The samples were resolved in 1 ml water when it was tested the items of PH value, biological activity and rhNRG-1 amount at the test interval.

The current specification is ≤3.0% residual moisture (as determined using the Karl Fischer Method). Lots rhNRG #1, rhNRG #2, rhNRG #3 and rhNRG #4 were released with moisture levels of 1.49%, 1.51%, 1.62%, and 1.35% respectively. Based on the past experience with other products with similar vial and stopper configurations, it is expected that any rhNRG-1 lots released with approximately 1.7% residual moisture will meet the specification limit of ≤3.0% at the end of the proposed shelf life (i.e. 24 months at the intended storage temperature of 5° C.±3° C.).

Long term stability studies at the recommended storage condition (i.e. 5° C.±3° C.) and elevated temperatures (i.e. 25° C.±2° C.) were conducted with four rhNRG-1 FDP lots that have been manufactured by Zensun. These studies have provided sufficient data to demonstrate the stability behavior of the individual clinical lots.

TABLE 17 storage condition & test interval of each batch

| Batch Number | Storage Conditions | Completed Test Intervals |
|---|---|---|
| rhNRG #1 | 5° C. ± 3° C. | 0, 3, 6, 9, 12, 18, 24 months |
|  | 25° C. ± 2° C. | 0, 1, 2, 4, 6 months |
| rhNRG #2 | 5° C. ± 3° C. | 0, 3, 6, 9, 12, 18, 24 months |
|  | 25° C. ± 2° C. | 0, 1, 2, 4, 6 months |
| rhNRG #3 | 5° C. ± 3° C. | 0, 3, 6, 9, 12, 18, 24 months |
|  | 25° C. ± 2° C. | 0, 1, 2, 4, 6 months |
| rhNRG #4 | 5° C. ± 3° C. | 0, 3, 6, 9, 12, 18, 24 months |
|  | 25° C. ± 2° C. | 0, 1, 2, 4, 6 months |

3. Results and Conclusions

Each batch was tested items including appearance, PH value, residual moisture, biological activity and rhNRG-1 amount at the test interval.

The stability protocol, including a description of the stability-indicating assays and stability-acceptance criteria, can be found in Table 18 which also contains information related to the rhNRG-1 FDP lots evaluated in the stability studies.

The results were listed in Table 18

TABLE 18

Stability testing results of each batch

| Storage Conditions acceptance criteria | Test time (Months) | Appearance White loose solid | PH value 6.0 ± 0.5 | Residual moisture <3.0% | Biological activity (U) 3500-10000 | rhNRG-1 amount (μg) 225-275 |
|---|---|---|---|---|---|---|
| \multicolumn{7}{c}{Stability data for rhNRG#1} |
| 5° C. ± 3° C. | 0 | conform | 5.98 | 1.49 | 4286 | 244 |
|  | 3 | conform | 6.01 | 1.85 | 4300 | 249 |
|  | 6 | conform | 6.02 | 1.93 | 4580 | 241 |
|  | 9 | conform | 6.01 | 2.15 | 4475 | 235 |
|  | 12 | conform | 6.03 | 2.26 | 4420 | 229 |
|  | 18 | conform | 6.04 | 2.37 | 4285 | 232 |
|  | 24 | conform | 6.03 | 2.62 | 4315 | 231 |
| 25° C. ± 2° C. | 1 | conform | 6.01 | 1.95 | 4870 | 242 |
|  | 2 | conform | 6.03 | 2.13 | 4650 | 239 |
|  | 4 | conform | 6.02 | 2.37 | 4430 | 238 |
|  | 6 | conform | 6.03 | 2.59 | 4543 | 234 |
| \multicolumn{7}{c}{Stability data for rhNRG#2} |
| 5° C. ± 3° C. | 0 | conform | 5.89 | 1.51 | 4220 | 247 |
|  | 3 | conform | 5.93 | 1.63 | 4040 | 252 |
|  | 6 | conform | 5.95 | 1.78 | 4645 | 248 |
|  | 9 | conform | 5.98 | 1.82 | 4500 | 237 |
|  | 12 | conform | 6.01 | 1.95 | 4450 | 233 |
|  | 18 | conform | 6.02 | 2.23 | 4728 | 234 |
|  | 24 | conform | 6.03 | 2.57 | 4285 | 232 |
| 25° C. ± 2° C. | 1 | conform | 5.95 | 1.98 | 4350 | 243 |
|  | 2 | conform | 6.01 | 2.23 | 4950 | 242 |
|  | 4 | conform | 6.03 | 2.35 | 4575 | 251 |
|  | 6 | conform | 6.03 | 2.51 | 4674 | 232 |
| \multicolumn{7}{c}{Stability data for rhNRG#3} |
| 5° C. ± 3° C. | 0 | conform | 5.92 | 1.62 | 4070 | 242 |
|  | 3 | conform | 5.97 | 1.71 | 4115 | 245 |
|  | 6 | conform | 5.95 | 1.82 | 4573 | 258 |
|  | 9 | conform | 5.98 | 1.95 | 4323 | 235 |
|  | 12 | conform | 6.01 | 2.03 | 4325 | 243 |
|  | 18 | conform | 6.02 | 2.25 | 4239 | 247 |
|  | 24 | conform | 6.01 | 2.37 | 4398 | 255 |
| 25° C. ± 2° C. | 1 | conform | 5.98 | 1.83 | 4125 | 241 |
|  | 2 | conform | 6.01 | 1.95 | 4539 | 252 |
|  | 4 | conform | 6.01 | 2.15 | 4378 | 245 |
|  | 6 | conform | 6.03 | 2.22 | 4585 | 259 |
| \multicolumn{7}{c}{Stability data for rhNRG#4} |
| 5° C. ± 3° C. | 0 | conform | 6.1 | 1.35 | 4797 | 248 |
|  | 3 | conform | 6.1 | 1.37 | 4809 | 252 |
|  | 6 | conform | 6.2 | 1.42 | 4982 | 253 |
|  | 9 | conform | 6.1 | 1.57 | 4756 | 255 |
|  | 12 | conform | 5.9 | 1.69 | 48/5 | 251 |
|  | 18 | conform | 6.2 | 1.83 | 4760 | 250 |
|  | 24 | conform | 6.3 | 2.12 | 4506 | 231 |
| 25° C. ± 2° C. | 1 | conform | 6.1 | 1.35 | 4587 | 249 |
|  | 2 | conform | 6.2 | 1.65 | 4621 | 251 |
|  | 4 | conform | 6.1 | 1.83 | 4588 | 250 |
|  | 6 | conform | 6.3 | 2.15 | 4844 | 253 |

The variation observed in residual moisture for lots rhNRG #1, rhNRG #2, rhNRG #3 and rhNRG #4 has remained well below the acceptance criterion ≤3.0%, and has not impacted the biological activity. There was no observable change in the stability results for qualitative analytical techniques (i.e. appearance, SDS-PAGE analysis, etc.) for the lots manufactured to be suitable for use in the non-clinical and clinical studies. Similarly, there was no trend in decreasing stability for the total protein analysis, the rhNRG-1 amount analysis during storage.

These rhNRG-1 FDP lots maintained rhNRG-1 biological activity for up to 24 months of storage at 5° C.±3° C. The results indicate stability at elevated temperature storage conditions for 6 months which can be extrapolated into a shelf life of more than 2 years under refrigerated conditions.

Proposed Storage Conditions and Shelf Life

The recommended storage condition for the rhNRG-1 FDP is 5° C.±3° C. A provisional shelf life of 24 months for the rhNRG-1 FDP is therefore proposed when stored at the recommended storage condition. The shelf life for the rhNRG-1 FDP lots likely can be further extended based on additional data to be generated for longer storage periods.

The above examples are included for illustrative purposes only and are not intended to limit the scope of the invention. Many variations to those described above are possible. Since modifications and variations to the examples described above will be apparent to those of skill in this art, it is intended that this invention be limited only by the scope of the appended claims.

What is claimed is:

1. A pharmaceutical formulation of neuregulin (NRG) comprising:
    (a) a polypeptide comprising the amino acid sequence set forth in SEQ ID NO: 2,
    (b) a buffering agent, wherein said formulation has a pH between 3 and 7, and
    (c) a stabilizing agent, wherein the stabilizing agent is human serum albumin at a concentration of about 8 g/L.

2. The formulation of claim 1, wherein the polypeptide consists of the amino acid sequence set forth in SEQ ID NO: 2.

3. The formulation of claim 1, wherein the concentration of the polypeptide is in a range of about 0.01 g/L to about 1 g/L.

4. The formulation of claim 3, wherein the polypeptide has a concentration of 0.25 g/L.

5. The formulation of claim 1, wherein the buffering agent is a pH buffering agent.

6. The formulation of claim 5, wherein the pH buffering agent is in a range of about 0.1 mM to about 500 mM.

7. The formulation of claim 5, wherein the buffering agent is selected from the group consisting of citrate, phosphate, acetate, histidine, glycine, bicarbonate, HEPES, Tris, diluted HCl, diluted NaOH and combinations of these agents.

8. The formulation of claim 7, wherein the buffering agent is phosphate.

9. The formulation of claim 8, wherein the pH is about 6.

10. The formulation of claim 8, wherein the pH is between 3 and 4.

11. The formulation of claim 1, wherein the formulation is a liquid formulation.

12. The formulation of claim 11, wherein the polypeptide consists of the amino acid sequence set forth in SEQ ID NO: 2.

13. The formulation of claim 11, wherein the buffering agent is phosphate.

14. The formulation of claim 11, wherein the polypeptide has a concentration of 0.25 g/L, wherein the buffering agent is 10 mM phosphate, and wherein said pH is about 3.4.

15. The formulation of claim 1, wherein the NRG formulation further comprises: (d) a salt.

16. The formulation of claim 15, wherein the salt is at a concentration range of about 100 mM to about 500 mM.

17. The formulation of claim 15, wherein the salt is sodium chloride.

18. The formulation of claim 17, wherein said sodium chloride is at a concentration of about 150 mM.

19. The formulation of claim 15, wherein the polypeptide has a concentration of about 0.25 g/L, wherein the buffering agent is phosphate at a concentration of about 10 mM, wherein said pH is about 6.0, wherein the stabilizing agent is human serum albumin at a concentration of about 2 g/L, and wherein the salt is sodium chloride at a concentration of about 150 mM.

20. A lyophilized pharmaceutical formulation of neuregulin (NRG), prepared by lyophilization of the formulation of claim 1 added with an excipient.

21. The formulation of claim 20, wherein the excipient is selected from the group consisting of human serum albumin, mannitol, glycine, polyethylene glycol, and combinations of these excipients.

22. The formulation of claim 20, wherein the excipient is at a concentration of about 0.1 g/L to about 200 g/L after resuspension of about 60 mg of the formulation with 1 ml of a resuspension solution.

23. The formulation of claim 20, wherein the excipient is mannitol.

24. The formulation of claim 23, wherein the mannitol is at a concentration of about 50 g/L after resuspension of about 60 mg of the formulation with 1 ml of a resuspension solution.

25. The formulation of claim 20, comprising phosphate as the buffering agent, mannitol as the excipient, and sodium chloride, wherein after resuspension of about 60 mg of the formulation with 1 ml of a resuspension solution, (a) the polypeptide is at a concentration of about 0.25 g/L;
 (b) the buffering agent is at a concentration of about 10 mM, and wherein the pH is about 6;
 (c) the excipient is at a concentration of about 50 g/L, and
 (d) the sodium chloride is at a concentration of about 150 mM.

26. The formulation of claim 25, wherein the resuspension solution is sterile deionized water or physiological saline.

* * * * *

SEQUENCE LISTING

<160> NUMBER OF SEQ ID NOS: 3

<210> SEQ ID NO 1
<211> LENGTH: 183
<212> TYPE: DNA
<213> ORGANISM: Homo sapiens

<400> SEQUENCE: 1

```
agccatcttg taaaatgtgc ggagaaggag aaaactttct gtgtgaatgg aggggagtgc     60
ttcatggtga agacctttc aaaccctcg agatacttgt gcaagtgccc aaatgagttt     120
actggtgatc gctgccaaaa ctacgtaatg gcgagcttct acaaggcgga ggagctgtac    180
cag                                                                  183
```

<210> SEQ ID NO 2
<211> LENGTH: 61
<212> TYPE: PRT
<213> ORGANISM: Homo sapiens

<400> SEQUENCE: 2

```
Ser His Leu Val Lys Cys Ala Glu Lys Glu Lys Thr Phe Cys Val Asn
1               5                   10                  15

Gly Gly Glu Cys Phe Met Val Lys Asp Leu Ser Asn Pro Ser Arg Tyr
            20                  25                  30

Leu Cys Lys Cys Pro Asn Glu Phe Thr Gly Asp Arg Cys Gln Asn Tyr
        35                  40                  45

Val Met Ala Ser Phe Tyr Lys Ala Glu Glu Leu Tyr Gln
    50                  55                  60
```

<210> SEQ ID NO 3
<211> LENGTH: 23
<212> TYPE: PRT
<213> ORGANISM: Homo sapiens

<400> SEQUENCE: 3

```
Ala Glu Lys Glu Lys Thr Phe Cys Val Asn Gly Gly Glu Cys Phe Met
1               5                   10                  15

Val Lys Asp Leu Ser Asn Pro
            20
```